(12) United States Patent
Aziz et al.

(10) Patent No.: US 12,283,423 B2
(45) Date of Patent: Apr. 22, 2025

(54) ASYMMETRIC SUPERCAPACITOR

(71) Applicant: KING FAHD UNIVERSITY OF PETROLEUM AND MINERALS, Dhahran (SA)

(72) Inventors: Md. Abdul Aziz, Dhahran (SA); Syed Shaheen Shah, Dhahran (SA); Yaqub Alhussain Mahnashi, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 148 days.

(21) Appl. No.: 18/363,389

(22) Filed: Aug. 1, 2023

(65) Prior Publication Data
US 2025/0046530 A1    Feb. 6, 2025

(51) Int. Cl.
| | |
|---|---|
| H01G 11/34 | (2013.01) |
| H01G 11/26 | (2013.01) |
| H01G 11/48 | (2013.01) |
| H01G 11/58 | (2013.01) |
| H01G 11/86 | (2013.01) |
| A61B 5/024 | (2006.01) |

(52) U.S. Cl.
CPC ............ *H01G 11/34* (2013.01); *H01G 11/26* (2013.01); *H01G 11/48* (2013.01); *H01G 11/58* (2013.01); *H01G 11/86* (2013.01); *A61B 5/024* (2013.01)

(58) Field of Classification Search
CPC ........ H01G 11/34; H01G 11/26; H01G 11/48; H01G 11/58; H01G 11/86; A61B 5/024
See application file for complete search history.

(56) References Cited

U.S. PATENT DOCUMENTS

| | | | | |
|---|---|---|---|---|
| 10,622,163 | B2 * | 4/2020 | Kaner | H01G 11/70 |
| 2002/0089807 | A1 * | 7/2002 | Bluvstein | H01G 11/70 |
| | | | | 361/302 |
| 2017/0033371 | A1 * | 2/2017 | Cordova | H01M 4/13 |

(Continued)

FOREIGN PATENT DOCUMENTS

| | | |
|---|---|---|
| CN | 106531471 A | 3/2017 |
| CN | 107747223 A | 3/2018 |

(Continued)

OTHER PUBLICATIONS

Divya et al. ; Renewable low cost green functional mesoporous electrode from Solanum lycopersicum leaves for supercapacitors ; Journal of Energy Storage vol. 27 ; Feb. 2020 ; 9 Pages.

(Continued)

*Primary Examiner* — Dion R. Ferguson
(74) *Attorney, Agent, or Firm* — Oblon, McClelland, Maier & Neustadt, L.L.P.

(57) ABSTRACT

The present disclosure provides an asymmetric supercapacitor that includes a negative electrode, a positive electrode, an ionic liquid electrolyte, and a separator. The negative electrode includes a tomato leaf activated carbon having a hierarchical porosity disposed on a first carbon cloth. The positive electrode includes a polyaniline disposed on a second carbon cloth; an ionic liquid electrolyte. The separator is located between the positive electrode and the negative electrode, and the ionic liquid electrolyte is present in and on the separator. The supercapacitor may be implemented in a heart pulse rate monitoring system.

20 Claims, 37 Drawing Sheets

(56) References Cited

U.S. PATENT DOCUMENTS

2017/0287650 A1   10/2017  Kaner et al.
2023/0238189 A1*  7/2023  Olabi .................. H01G 11/24
                                                          427/79
2025/0046530 A1*  2/2025  Aziz .................... H01G 11/34

FOREIGN PATENT DOCUMENTS

CN        209149956 U      7/2019
CN        111363146 A  *  7/2020  ......... C08G 73/0266

OTHER PUBLICATIONS

Lobato-Peralta et al. ; Sustainable production of self-activated bio-derived carbons through solar pyrolysis for their use in supercapacitors ; Journal of Analytical and Applied Pyrolysis vol. 150 ; Sep. 2020 ; 3 Pages ; Abstract Only.
Martha ; Carotenoid-like Lycopene extracted from tomato as an efficient electrode for high-specific capacitance and high power density of supercapacitors ; Journal of Materials Science: Materials in Electronics 32 ; Apr. 29, 2021 ; 14 Pages ; Abstract Only.
Hekmat et al. ; Hybrid energy storage device from binder-free zinc-cobalt sulfide decorated biomass-derived carbon microspheres and pyrolyzed polyaniline nanotube-iron oxide ; Energy Storage Materials vol. 25 ; Mar. 2020 ; 10 Pages.

* cited by examiner

ASYMMETRIC SUPERCAPACITOR

STATEMENT REGARDING PRIOR DISCLOSURE BY THE INVENTORS

Aspects of the present disclosure were described in an article titled "A High-Energy Asymmetric Supercapacitor Based on Tomato-Leaf-Derived Hierarchical Porous Activated Carbon and Electrochemically Deposited Polyaniline Electrodes for Battery-Free Heart-Pulse-Rate Monitoring" published in Small on Apr. 24, 2023, and corresponding Supporting Information at DOI: 10.1002/smll.202300258, both of which are incorporated herein by reference in their entireties.

STATEMENT OF ACKNOWLEDGEMENT

The inventors acknowledge the support provided by the Interdisciplinary Research Center for Hydrogen and Energy Storage, King Fahd University of Petroleum and Minerals, Saudi Arabia, through Project INHE2105.

BACKGROUND

Technical Field

The present disclosure relates to high-performance energy storage devices and more particularly relates to asymmetric capacitors.

Discussion of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

Electrochemical capacitors (ECs) may be configured to store several hundred times more energy per unit weight (gravimetric energy density) and per unit volume (volumetric energy density) as compared to traditional electrolytic capacitors. Hereinafter energy density refers to both gravimetric and volumetric energy density. Additional advantages of ECs include high cycle life (>300,000 cycles), high discharge rates (from minutes to milliseconds), safety tolerance to high-rate charge, discharge, overcharge, wide operating temperatures, and good state-of-charge indication during charge and discharge. In many cases ECs can exceed the performance of batteries in applications requiring high power density and discharge rates that are in the minutes to seconds range, such as those encountered in pulse discharge applications.

Electrochemical double layer capacitors, also known as supercapacitors, store energy by a charging of the electrode/electrolyte interface (double layer capacitance) or through faradaic reactions (pseudocapacitance) occurring at or near the electrode surface. Active materials, which function as electrode materials for these supercapacitors, include activated carbons (typically having surface areas in the range of 1000 to 3000 $m^2/g$), mixed metal oxides (for example, ruthenium oxide and iridium oxide), and doped conductive polymers, such as polypyrrole and polyaniline. Both aqueous and non-aqueous electrolytes are known to be used.

Supercapacitors are electrochemical energy storage technologies with a potential to meet various energy storage application requirements. The technique by which a supercapacitor stores a charge divides it into two subcategories: electrochemical double-layer capacitors (EDLCs) and pseudocapacitors. Contrary to the capacitance of EDLCs, which is often brought on by an accumulation of electrolyte ions at the electrode/electrolyte interface, pseudocapacitance is usually brought on by reversible faradic processes. The primary electroactive materials for EDLCs are carbon, including activated carbon, carbon aerogel, carbon nanotubes (CNTs), carbon nanofibers, and graphene. Activated carbon materials are ideal for EDLCs due to multiple advantages, such as high specific surface area (SSA), physicochemical stability, excellent conductivity, low cost, and low density. Specifically, activated carbon, which exhibits high SSA, and carbon nanosheets architecture have high electrical conductivity, abundant electrocatalytic active sites, and desirable surface hydrophilicity. This facilitates better electrolyte/electrode interaction which make activated carbon and carbon nanosheets ideal for fast charge transfer and storage. However, most activated carbon materials are derived from non-renewable oil sources and, due to the growing public awareness of pollution control, are of concern. Alternative sources of carbon, such as biomass-derived activated carbon, is preferred. This is due to the low cost, biocompatibility, sustainability, and abundance, renewable resources, such as biomass (including tomato leaves), are substitutes for creating porous carbons. For the mass production of ecologically benign and economically viable porous activated carbon for supercapacitors, biomass sources are raw materials with promise. Despite their numerous benefits, the specific capacitance of carbon materials must be increased to meet the future demands for high-performance supercapacitors.

Typically, conductive polymers, such as polyaniline (PANI), polythiophene, and polypyrrole are employed in the fabrication of electrode materials for pseudocapacitors. PANI has great promise for use in supercapacitors because of its inexpensive cost, outstanding environmental stability, simplicity of synthesis, rapid redox rate, relatively high degree of electrical conductivity, and novel doping-dedoping chemistry. However, the expansion and contraction of PANI caused by the addition and removal of counter ions causes a volume change and weakens the polymer's structural support. This structure degradation reduces the charging/discharging cyclic life, thereby restricting its supercapacitor applications [See: T. Liu, L. Finn, M. Yu, H. Wang, T. Zhai, X. Lu, Y. Tong, Y. Li, Nano Lett. 2014, incorporated herein by reference in its entirety]. Carbon/PANI composites are provided to address issues with the EDLCs and pseudocapacitors, as such composites integrate the electrostatic charge accumulation and faradic response mechanisms. Examples of such composites include PANI@graphene, PANI@CNTs, and PANI@carbon nanofibers. However, these carbons have limited practical applications due to their high cost and complex synthesis. Consequently, the electrochemical deposition of PANI on carbon cloth (CC) could provide a pathway for the synthesis of low-cost flexible supercapacitor electrodes.

Based on the electrode configurations, supercapacitors are classified as symmetric and asymmetric. In a symmetric supercapacitor, both electrodes are constructed from the same material, while in an asymmetric supercapacitor, the electrodes are composed of different materials. The symmetric supercapacitors employ materials having approximately the same level of response to an applied voltage for both electrodes, whereas asymmetric supercapacitors utilize two different materials for the electrodes. The electrodes in an asymmetric supercapacitor each have a differing magnitude of response to an applied voltage. Alternatively, symmetric supercapacitors use the same mechanism of energy storage at both electrodes while asymmetric supercapacitors use different mechanisms of energy storage at each electrode.

Electrolytes are an active component of supercapacitors and include aqueous electrolytes, solid electrolytes, and ionic liquid electrolytes. Due to the flexibility and mobility of ions, ionic liquids offer a wide potential in the field of electrochemistry. Although ionic liquids function as substitutes for solvents or electrolytes, their uses in electrochemical systems are more than basic solvents and electrolytes. Ionic liquids are not solvents but rather a mobile ion matrix, similar to molten salts in electrochemistry [See: A. Eftekhari, *Energy Storage Mater.* 2017, incorporated herein by reference in its entirety]. Various potential applications of ionic liquids in supercapacitors and novel design options for electrolytes have been studied. Increasing the electrode capacity or the device's operating potential window (OPW) may increase a supercapacitor's energy density. Increasing the OPW, which is primarily determined by the stability of the electrolyte, results in an effect on the energy density of the supercapacitors. Due to higher OPW, electrolytes based on ionic liquids are preferred over aqueous electrolytes for achieving higher energy densities [See: K. L. Van Aken, M. Beidaghi, Y. Gogotsi, *Angew. Chem. Int. Ed.* 2015, incorporated herein by reference in its entirety]. The voltage stability window predicted for ionic liquid electrolytes is smaller than the maximum OPW of the device when a supercapacitor is built using such electrolytes. This is the case for ionic liquid electrolytes, which can maintain their stability in the range of 5 V to 6 V. Therefore, ionic liquid electrolytes may provide a wider OPW for producing supercapacitors with ultra-high energy density.

Accordingly, an object of the present disclosure to develop a tomato leaves-derived hierarchical porous activated carbon network (TAC) and polyaniline (PANI)-based asymmetric supercapacitor with exceptional electrochemical performance in an ionic liquid electrolyte.

SUMMARY

In one exemplary embodiment, an asymmetric supercapacitor is disclosed. The asymmetric supercapacitor includes a negative electrode having a tomato leaf activated carbon having a hierarchical porosity disposed on a first carbon cloth: a positive electrode having a polyaniline disposed on a second carbon cloth: an ionic liquid electrolyte; and a separator. The separator is located between the positive electrode and the negative electrode, and the electrolyte is present in and on the separator.

In some embodiments, the tomato leaf activated carbon has a specific surface area of 1400 square meters per gram ($m^2/g$) to 1500 $m^2/g$.

In some embodiments, the tomato leaf activated carbon is in the form of nanosheets having a pore size distribution of 1 nanometer (nm) to 200 nm.

In some embodiments, the negative electrode is made by a process including rinsing tomato leaves, drying the tomato leaves, pulverizing the tomato leaves, mixing the tomato leaves with a base to form a first reaction mixture, and heating the first reaction mixture in a tube furnace at 850° C. for at least 5 hours under a nitrogen atmosphere with a heating rate of 10° C./minute and a cooling rate of 5° C./minute to form a reaction product. The process further includes washing the reaction product, drying the reaction product to form the tomato leaf activated carbon, sonicating the tomato leaf activated carbon in a solution with a polyvinylidene fluoride polymer and an N-methyl-2-pyrrolidone to form a second reaction mixture, and drop-casting the second reaction mixture onto the first carbon cloth and drying to form the negative electrode. In some embodiments, the solution includes aniline and sulfuric acid.

In some embodiments, a ratio of the tomato leaf activated carbon to the polyvinylidene fluoride in the N-methyl-2-pyrrolidone is 85:15 percent weight by weight to 95:5 percent weight by weight.

In some embodiments, a working area of drop-casting the second reaction mixture onto the first carbon cloth is 0.5 square centimeters ($cm^2$) to 1.5 $cm^2$.

In some embodiments, the polyaniline on the second carbon cloth has a nodular morphology with void spaces having an average diameter of 5 micrometers ($\mu m$) to 500 $\mu m$ and polyaniline nanoparticles having an average diameter of 0.05 $\mu m$ to 0.5 $\mu m$ uniformly distributed on carbon cloth fibers having an average diameter of 1 $\mu m$ to 10 $\mu m$.

In some embodiments, the positive electrode is made by a process electrodepositing the polyaniline on the second carbon cloth with cyclic voltammetry for 15 cycles at a scan rate of 50 millivolts per second (mV/sec) in a window of 0.0 volts (V) to 1.0 V vs Ag/AgCl; rinsing the polyaniline on the second carbon cloth; and drying the polyaniline on the second carbon cloth.

In some embodiments, the electrodepositing includes electrodepositing the polyaniline on a target area of the second carbon cloth of 0.5 $cm^2$ to 1.5 $cm^2$.

In some embodiments, the ionic liquid electrolyte is 1-butyl-3-methylimidazolium hexafluorophosphate.

In some embodiments, a first electrode is the negative electrode comprising a tomato leaf activated carbon having a hierarchical porosity disposed on the first carbon cloth and a second electrode is the positive electrode comprising a polyaniline disposed on the second carbon cloth.

In some embodiments, the separator is a cellulose membrane soaked in the ionic liquid electrolyte.

In some embodiments, the supercapacitor has an areal capacitance of 230 millifarad per square centimeters ($mF/cm^2$) to 270 $mF/cm^2$ at a scan rate of 50 mV/sec.

In some embodiments, the supercapacitor has an energy density of 240 microwatt hour per square centimeters ($\mu Wh/cm^2$) to 280 $\mu Wh/cm^2$ at a power density of 1300 $\mu W/cm^2$ to 2900 $\mu Wh/cm^2$.

In some embodiments, the supercapacitor has a capacitance retention after 10,000 charge-discharge cycles of at least 95% of a first charge-discharge cycle.

In some embodiments, the supercapacitor has a Coulombic efficiency of at least 98% after 10,000 charge-discharge cycles at a current density of 10 milliampere per square centimeters ($mA/cm^2$).

In some embodiments, an operating potential window is from −0.5 V to 3.5 V.

In another exemplary embodiment, a heart pulse rate monitoring system is provided. The heart pulse rate monitoring system includes one or more of the supercapacitor, a microcontroller, a sensor, and a charge controller.

In some embodiments, the charge controller is a solar panel, a solar energy harvesting chip, or a combination thereof.

In some embodiments, the heart pulse rate monitoring system operates continuously for at least 20 minutes.

These and other aspects of non-limiting embodiments of the present disclosure will become apparent to those skilled in the art upon review of the following description of specific non-limiting embodiments of the disclosure in conjunction with the accompanying drawings.

BRIEF DESCRIPTION OF THE DRAWINGS

A better understanding of embodiments of the present disclosure (including alternatives and/or variations thereof) may be obtained with reference to the detailed description of the embodiments along with the following drawings, in which:

FIG. 2I is a FESEM micrograph of TAC on CC (TAC@CC) at 1000× magnification, according to an aspect of the present disclosure;

DETAILED DESCRIPTION

Figure 1A:
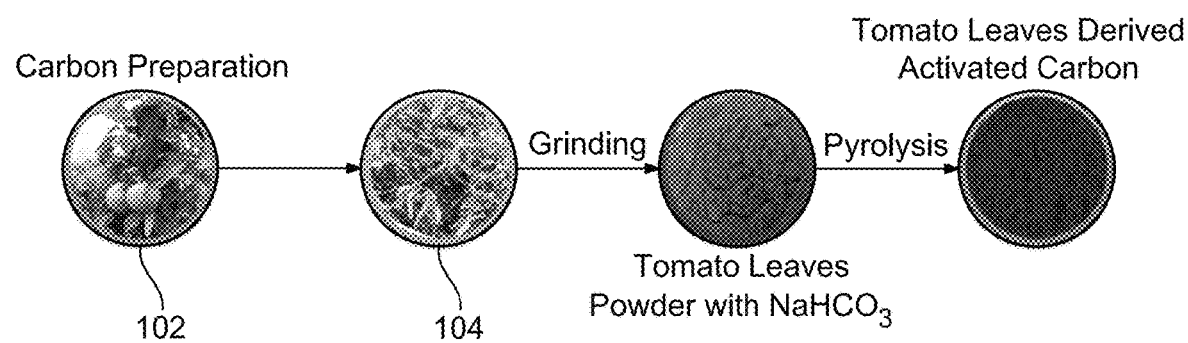
FIG. 1A is a schematic representation of preparation of tomato leaves derived activated carbon (TAC), according to an aspect of the present disclosure.

In the following description, it is understood that other embodiments may be utilized, and structural and operational changes may be made without departure from the scope of the present embodiments disclosed herein.

Reference will now be made in detail to specific embodiments or features, examples of which are illustrated in the accompanying drawings. Wherever possible, corresponding, or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of the present disclosure relate to an asymmetric supercapacitor. A simple and scalable method to fabricate a high-energy asymmetric supercapacitor using tomato leaves-derived hierarchical porous activated carbon network (TAC) and electrochemically deposited polyaniline (PANI) for battery-less heart pulse rate monitor is also provided. Due to the interconnected network and high porosity, the TAC was selected as an electrode material for asymmetric supercapacitors containing ionic liquid-based electrolyte to provide ultra-high energy density.

In a preferred embodiment, the ionic liquid-based electrolyte contains an ionic liquid, preferably 1-butyl-3-methylimidazolium hexafluorophosphate. In some embodiments, the ionic liquid-based electrolyte may be in the form of a liquid, solid, or a gel. In some embodiments, the electrolyte is a solution with a uniform dispersion of cations and anions. A solution matrix may be an ionic liquid. Although electrolytes are neutral in charge, applying an electrical potential (voltage) to the solution draws the cations of the solution to the electrode with an abundance of electrons, and the anions to the electrode with a deficit of electrons. As such, the movement of cations and anions in opposite directions within the same solution forms an energy current. Ions are transferred between the electrodes and the electrolyte efficiently due to the strong ionic conductivity of ionic liquids, which enhance performance and raise specific capacitance. Ionic liquids can maintain a steady and consistent voltage range over a wide variety of charges and a large electrochemical window. Ionic liquids are non-volatile and do not readily evaporate, in contrast to organic electrolytes. Ionic liquids have a long service life and dependability due to their high chemical stability and resistance to oxidation, reduction, and other chemical processes. Ionic liquids are eco-friendly replacements for organic electrolytes due to biodegradability and relative non-toxicity. The wide electrochemical window, strong ionic conductivity, non-volatility, chemical stability, and environmentally favorable characteristics of ionic liquid electrolytes make their use well suited for the supercapacitors of the present disclosure.

In accordance with the aspects of the present disclosure, the TAC was prepared by simple pyrolysis, and exhibited nanosheet-type morphology and a high specific surface area of about 1440 m$^2$/g. The TAC can be drop-cast onto flexible carbon cloth (CC) to fabricate the TAC@CC electrode, whereas PANI can be electrochemically deposited onto CC to fabricate the PANI@CC electrode. The TAC@CC (as a negative electrode) and PANI@CC (as a positive electrode) based asymmetric supercapacitor showed good electrochemical performance in ionic liquid electrolyte. A current collector of carbon cloth, stainless steel, crucible steel, carbon steel, spring steel, alloy steel, maraging steel, weathering steel, tool steel, of any combination thereof may be used. The electrochemical performance demonstrated that the TAC@CC and PANI@CC electrodes based asymmetric supercapacitor exhibited greater supercapacitor behavior than a TAC@CC symmetric supercapacitor or a PANI@CC symmetric supercapacitor.

According to the present disclosure, an asymmetric supercapacitor is described. The asymmetric supercapacitor includes two electrodes, namely a negative electrode or a first electrode and a positive electrode or a second electrode. The negative electrode and the positive electrode are collectively referred to as 'the electrodes' unless otherwise specifically mentioned. The negative electrode includes a tomato leaf activated carbon (TAC) material having a hierarchical porosity disposed on a first carbon cloth, while the positive electrode includes polyaniline (PANI) disposed on a second carbon cloth. The hierarchical porosity comprises different pore sizes in a porous structure. The hierarchical porosity of the TAC material includes a combination of micropores, mesopores, and/or macropores. Micropores have a pore diameter of less than 2 nm, mesopores have a pore diameter of 2 to 50 nm, and macropores have a pore diameter of greater than 50 nm. A cumulative pore volume for the micropores is 0.5 to 2.0 cm$^3$/g, preferably 0.6 to 1.0 cm$^3$/g, and more preferably 0.7 to 1.0 cm$^3$/g. A cumulative pore volume for the mesopores is 0.1 to 1.0 cm$^3$/g, preferably 0.2 to 0.9 cm$^3$/g, and more preferably 0.2 to 0.8 cm$^3$/g. A cumulative pore volume for the macropores is 0.01 to 1.0 cm$^3$/g, preferably 0.01 to 0.5 cm$^3$/g, and more preferably 0.1 to 0.4 cm$^3$/g. The TAC material includes a hierarchical porosity with pore sizes ranging from less than 1 to 1000 nm, preferably less than 1 to 500 nm, and more preferably less than 1 to about 200 nm. The combination of micropores, mesopores, and/or macropores promote facile electrolyte diffusion through the pores and increase the performance of the asymmetric supercapacitor. The TAC material comprises nanosheets which are drop-cast onto the first carbon cloth. The first carbon cloth may have a thickness of 100 to 500 microns, preferably 200 to 500 microns, and more preferably 300 to 400 microns. The film made by drop-casting of the TAC material onto the first carbon cloth may be more or less thick than the thickness of the carbon cloth, preferably less thick, and may be varied depending on the amount of TAC material that is drop-casted. In an embodiment, the thickness of the TAC material may be 0.01 to 1000 microns, preferably 0.1 to 500 microns, more preferably 0.1 to 100 microns, and yet more preferably 0.1 to 10 microns.

The TAC material comprising nanosheets present in the film/coating covering the carbon cloth may be in layers. The layers may be formed from overlapping smaller flakes of the TAC material. The overlapping flakes may be 10 to 1000 nm in diameter, preferably 100 to 800 nm, and more preferably 100 to 500 nm. The overlapping flakes may form in one or more layers with one or more concave surfaces and one or more convex surfaces. The one or more concave surfaces may have a depth of 1 to 100 nm, preferably 5 to 50 nm, and more preferably 10 to 20 nm (see for example FIGS. 5A and 5C). The one or more convex surfaces may have a height of 1 to 100 nm, preferably 1 to 50 nm, and more preferably 1 to 20 nm, and a largest diameter measured at the base of 5 to 100 nm, preferably 10 to 50 nm, and more preferably 20 to 40 nm.

The polyaniline disposed on the second carbon cloth forms a film having a nodular morphology with void spaces having an average diameter of 1 to 1000 microns, preferably 5 to 500 microns, and more preferably 10 to 200 microns. The void spaces may be three-dimensional spaces in the shape of a crack, a sphere, a cube, a rhombus, an amorphous shape, and the like. The polyaniline disposed on the second carbon cloth comprises polyaniline nanoparticles having an average largest diameter of 0.01 to 10 microns, preferably 0.1 to 5 microns, and more preferably 0.1 to 1 micron, and yet more preferably 0.05 to 0.5 microns. A plurality of polyaniline nanoparticles may form aggregate conglomerations in the form of branches, ridges, spheres, amorphous shapes, and the like. The second carbon cloth may have a thickness of 100 to 500 microns, preferably 200 to 500 microns, and more preferably 300 to 400 microns. The electrodeposition of the polyaniline may form a polyaniline film on the second carbon cloth that may more thick or less thick than the thickness of the carbon cloth, preferably less thick, and may be varied depending on the amount of PANI that is electrodeposited and the duration of the electrodeposition. In an embodiment, the thickness of the PANI may be 0.01 to 1000 microns, preferably 0.1 to 500 microns, more preferably 0.1 to 100 microns, and yet more preferably 0.1 to 10 microns. The polyaniline nanoparticles may be uniformly distributed on carbon cloth fibers, in which the carbon cloth fibers may have an average diameter of 1 to 10 microns, preferably 3 to 8 microns, and more preferably about 5 microns.

The asymmetric supercapacitor further includes a separator, placed between the positive electrode and the negative electrode. The separator is preferably a cellulose membrane soaked in a ionic liquid electrolyte. In an embodiment, the separator is a cellulose membrane filter paper. The ionic liquid electrolyte is present in and on the separator. In an embodiment, the ionic liquid electrolyte is 1-butyl-3-methylimidazolium hexafluorophosphate.

A method of preparing a negative electrode is described, according to an embodiment of the present disclosure. The method includes the following steps:

Step 1: The tomato leaves were rinsed 1 to 20 times, preferably 1 to 10 times, and more preferably 3 to 10 times with distilled water to remove any contaminants.

Step 2: The rinsed tomato leaves were further dried in an oven at 80 to 140° C., preferably 90 to 130° C., more preferably 95 to 120° C., and yet more preferably about 100° C., to reduce the moisture content to below 5 percent by weight (wt. %), preferably below 4 wt. %, preferably below 3 wt. %, more preferably below 2 wt. %, and yet more preferably below 1 wt. %. The tomato leaves may be dried for any amount of time that provides an adequately dried product (dry tomato powder), typically, for drying times of 10 to 30 hours, preferably 12 to 20 hours, and more preferably about 12 hours.

Step 3: The dried tomato leaves were further pulverized to form a powder or leaves with smaller particle sizes. Pulverization may be carried out using any suitable means, for example, by grinding, ball milling, blending, and the like, using manual methods (e.g., mortar and pestle) or machine-assisted methods such as using a mechanical blender, or any other apparatus known to those of ordinary skill in the art. The dried tomato leaves are preferably pulverized until an average particle size of less than 50 µm, preferably less than 40 µm, more preferably less than 30 µm, and yet more preferably less than 20 µm is achieved.

Step 4: The pulverized tomato leaves were further mixed with a base, such as sodium bicarbonate, to form a first reaction mixture. In some embodiments, the pulverization may be carried out in the presence of other bases, such as sodium hydroxide, potassium bicarbonate, cesium bicarbonate, magnesium bicarbonate, calcium bicarbonate, potassium hydroxide, manganese hydroxide, and calcium hydroxide to obtain the first reaction mixture.

Step 5: The first reaction mixture was further heated in a tube furnace at 850° C. for at least 5 hours under a nitrogen atmosphere with a heating rate of 10° C./minute and a cooling rate of 5° C./minute to form a reaction product. Pyrolysis is a process of thermochemical decomposition at elevated temperatures and occurs in the absence of an oxidizing agent such as oxygen, hydrogen peroxide, and/or a halogen-containing gas (e.g., a chlorine-containing gas). In some embodiments, pyrolysis is performed in an inert gas environment (e.g., nitrogen, helium, neon, argon, and/or a combination thereof), preferably nitrogen, and in a temperature range of 700 to 1,000° C., preferably 725 to 975° C., preferably 750 to 950° C., preferably 775 to 925° C., preferably 800 to 900° C., more preferably 825 to 875° C., and yet more preferably about 850° C. Pyrolysis of the first reaction mixture preferably forms a solid, for example, a carbonaceous ash/char/tar that mainly contains carbon and heteroatoms (e.g. nitrogen, oxygen), along with silicon, and in some cases, minor amounts of other elements and minerals such as aluminum, iron, calcium, magnesium, potassium, sodium, and the like. The pyrolysis of the pulverized tomato leaves may also form volatile compounds, which may evaporate during the pyrolysis. In some embodiments, pyrolysis may be performed by placing the first reaction mixture into a furnace such as a tube furnace, for example, in a ceramic crucible (e.g., an alumina crucible) or other forms of containment, and heating to the temperatures described above. The furnace is preferably equipped with a temperature control system, which may provide a heating rate of up to 50° C./min, or preferably up to 40° C./min, or preferably up to 30° C./min, preferably up to 20° C./min, preferably up to 10° C./min. The heating rate may be adjustable. The furnace may also be equipped with a cooling accessory such as a cooling air stream system, or a liquid nitrogen stream system, which may provide a cooling rate of up to 20° C./min, or preferably up to 15° C./min, or preferably up to 10° C./min, or preferably up to 5° C./min, to form the reaction product. The cooling rate may be adjustable.

Step 6: The reaction product is further washed with acid to remove any impurities followed by water to remove any excess acid. In an embodiment, the acid is acetic acid. In an embodiment, the water is deionized (DI) water. The washed reaction product is further dried to remove moisture. In an embodiment, the reaction product is dried to a temperature range of 80 to 100° C., to form the tomato leaf activated carbon (TAC). The TAC has a specific surface area of 1000 to 2000 $m^2/g$, preferably 1200 to 1800 $m^2/g$, and more preferably about 1400 to 1500 $m^2/g$. The TAC may be in the form of nanosheets having an amorphous morphology with a pore size distribution of 0.1 to 1000 nm, preferably 0.5 to 500 nm, and more preferably 1.0 to 200 nm.

Step 7: The TAC is further sonicated in a solution with a polyvinylidene fluoride (PVDF) polymer and an N-methyl-2-pyrrolidone (NMP) for 1 to 12 hours, preferably 1 to 10 hours, more preferably 1 to 5 hours, and yet more preferably about 1 hour to form a second reaction mixture. The PVDF serves as a binder, while the NMP serves as a solvent. Optionally other binders, such as polyvinylidene chloride, hexafluoropropylene (HFP), polyethylene, polypropylene, polystyrene, polyethylene terephthalate, or binders known in the art, may be used as well. Similarly, other solvents, such as acetonitrile or water, may be used instead of NMP. The binder helps particle dispersion in the solvent and helps to deliver a uniform slurry and discrete particles on the electrode. In some embodiments, the ratio of TAC to PVDF/binder is a weight ratio of 85:15 percent weight by weight to 95:5, preferably 90:10. Any agitation method known to those of ordinary skill in the art, for example, via stirring, swirling, mixing, or sonicating (e.g., ultrasonication or sonication) may be used as well.

Step 8: The second reaction mixture is drop-casted onto a first carbon cloth and dried to form the negative electrode. The second reaction mixture is further drop-casted onto an electrode, preferably a carbon electrode, and dried to form the negative electrode. In a preferred embodiment, the carbon electrode is a carbon cloth electrode. In some embodiments, the electrode may be a functionalized carbon electrode, an activated carbon electrode, a carbon paper electrode, a carbon fiber electrode, an amorphous carbon electrode, a glassy carbon electrode, a carbon nanofoam electrode, a carbon aerogel electrode, and the like. A working area of drop-casting the second reaction mixture onto the first carbon cloth is 0.1 to 2.0 $cm^2$, preferably 0.5 to 1.5 $cm^2$, and more preferably about 1.0 $cm^2$. The second reaction mixture drop-cast onto the carbon cloth is dried in an oven at a temperature of 50 to 100° C., preferably 70 to 90° C., and more preferably about 80° C. for a time of 1 to 24 hours, preferably 6 to 18 hours, and more preferably about 12 hours.

A method of preparing a positive electrode is described, according to an embodiment of the present disclosure. Polyaniline (PANI) was electrodeposited by potentiostaic oxidation of an aniline monomer in an aqueous solution of sulfuric acid onto a second carbon cloth electrode. In a preferred embodiment, the aniline monomer is aniline. In some embodiments, the aniline monomer may be a substituted aniline monomer or functionalized aniline monomer. In an embodiment, the concentration of the aniline monomer is 0.1 to 2.0 M, preferably 0.1 to 1.0 M, and more preferably about 0.5 M. In an embodiment, the concentration of sulfuric acid is 0.1 to 2.0 M, preferably 0.5 to 2.0 M, and more preferably about 1.0 M. Optionally, other electrodes, such as glassy carbon electrode or carbon electrode may be used as well. The electrodeposition is carried out with a three-electrode system. In a preferred embodiment the working electrode is a carbon cloth, the counter electrode is a platinum wire, and the reference electrode is an Ag/AgCl electrode. The electrodeposition is carried out with cyclic voltammetry for 10 to 30 cycles, preferably, 10 to 20 cycles, and more preferably about 15 cycles at a scan rate of 10 to 200 mV/sec, preferably 20 to 100 mV/sec, and more preferably about 50 mV/sec in a window of 0.0 V to 1.0 V vs Ag/AgCl. The PANI is electrodeposited on a target area of the second carbon cloth of 0.1 to 2.0 $cm^2$, preferably 0.5 to 1.5 $cm^2$, and more preferably about 1.0 $cm^2$. Morphological analysis of the polyaniline on the second carbon cloth shows a nodular morphology with void spaces having an average diameter of 5 μm to 500 μm and polyaniline nanoparticles having an average diameter of 0.05 μm to 0.5 μm uniformly distributed on carbon cloth fibers having an average diameter of 1 μm to 10 μm. After electrodeposition, the electrode is washed several times with distilled water/de-ionized water to remove any acids. The washed electrode is further dried at room temperature to form PANI@CC electrode.

The supercapacitor of the present disclosure has an areal capacitance of 230 $mF/cm^2$ to 270 $mF/cm^2$ at a scan rate of 50 mV/sec: an energy density of 240 μWh/$cm^2$ to 280 μWh/$cm^2$ at a power density of 1300 μW/$cm^2$ to 2900 μWh/$cm^2$: a capacitance retention after 10,000 charge-discharge cycles of at least 95% of a first charge-discharge cycle; and a Coulombic efficiency of at least 98% after 10,000 charge-discharge cycles at a current density of 10 mA/$cm^2$ at an operating potential window from −1.0 to 5.0

V, preferably −0.5 to 4.0 V, more preferably −0.5 to 3.5 V, and yet more preferably 0.0 to 3.0 V.

The asymmetric supercapacitor with the negative electrode of TAC@CC and the positive electrode of PANI@CC demonstrates higher areal capacitance, energy density, and power density than a symmetric supercapacitor comprising solely TAC@CC or solely PANI@CC. In a symmetric supercapacitor, both the positive and negative electrodes comprise the same materials. A symmetric supercapacitor comprising two electrodes of TAC@CC demonstrates pseudocapacitor behavior and a symmetric supercapacitor comprising two electrodes of PANI@CC demonstrates electrochemical double layer capacitor behavior. The asymmetric supercapacitor demonstrates a hybrid supercapacitor-type behavior and outperforms both symmetric supercapacitors described above. The asymmetric supercapacitor demonstrates a synergistic effect of the TAC@CC with the PANI@CC. For example, at a power density of 2800 $\mu W/cm^2$, the asymmetric supercapacitor demonstrates an energy density of about 251 $\mu Wh/cm^2$, while the symmetric supercapacitors of TAC@CC and PANI@CC demonstrate an energy density of about 210 $\mu W/cm^2$ and about 164 $\mu W/cm^2$, respectively, at the same power density. The amount of TAC@CC in a symmetric supercapacitor may be about double the amount of TAC@CC in the asymmetric supercapacitor. The amount of PANI@CC in a symmetric supercapacitor may be about double the amount of PANI@CC in the asymmetric supercapacitor. The performance of the supercapacitor of the current disclosure is improved with the use of TAC@CC as the negative electrode and PANI@CC as the positive electrode over the performance of the TAC@CC symmetric capacitor and PANI@CC symmetric capacitor.

In some embodiments, the supercapacitor may be attached to a wearable device and function as a battery to provide electric power to various components of the wearable device. Particularly, the supercapacitor may be electrically connected to a sensor, thereby facilitating the sensor to detect various operating conditions or parameters of the wearable device. In an example, the wearable device may be a wristwatch. In some examples, the wearable device may be any device that may be deriving power from a power source such as a battery: as such, the supercapacitor of the present disclosure may be implemented in the device to function as a battery.

EXAMPLES

Figure 1B:
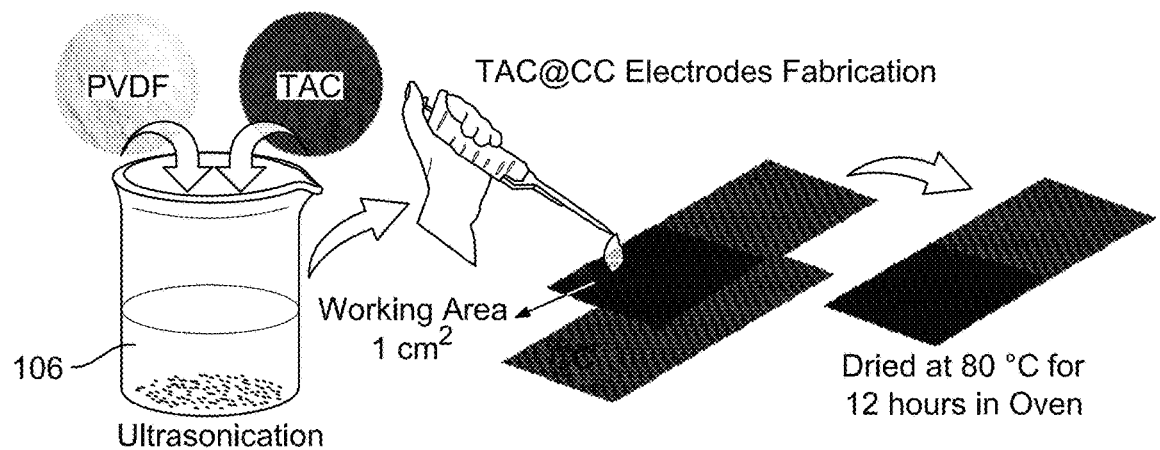
FIG. 1B is a schematic representation of fabrication of a negative supercapacitor electrode using TAC, according to an aspect of the present disclosure.
Figure 1C:
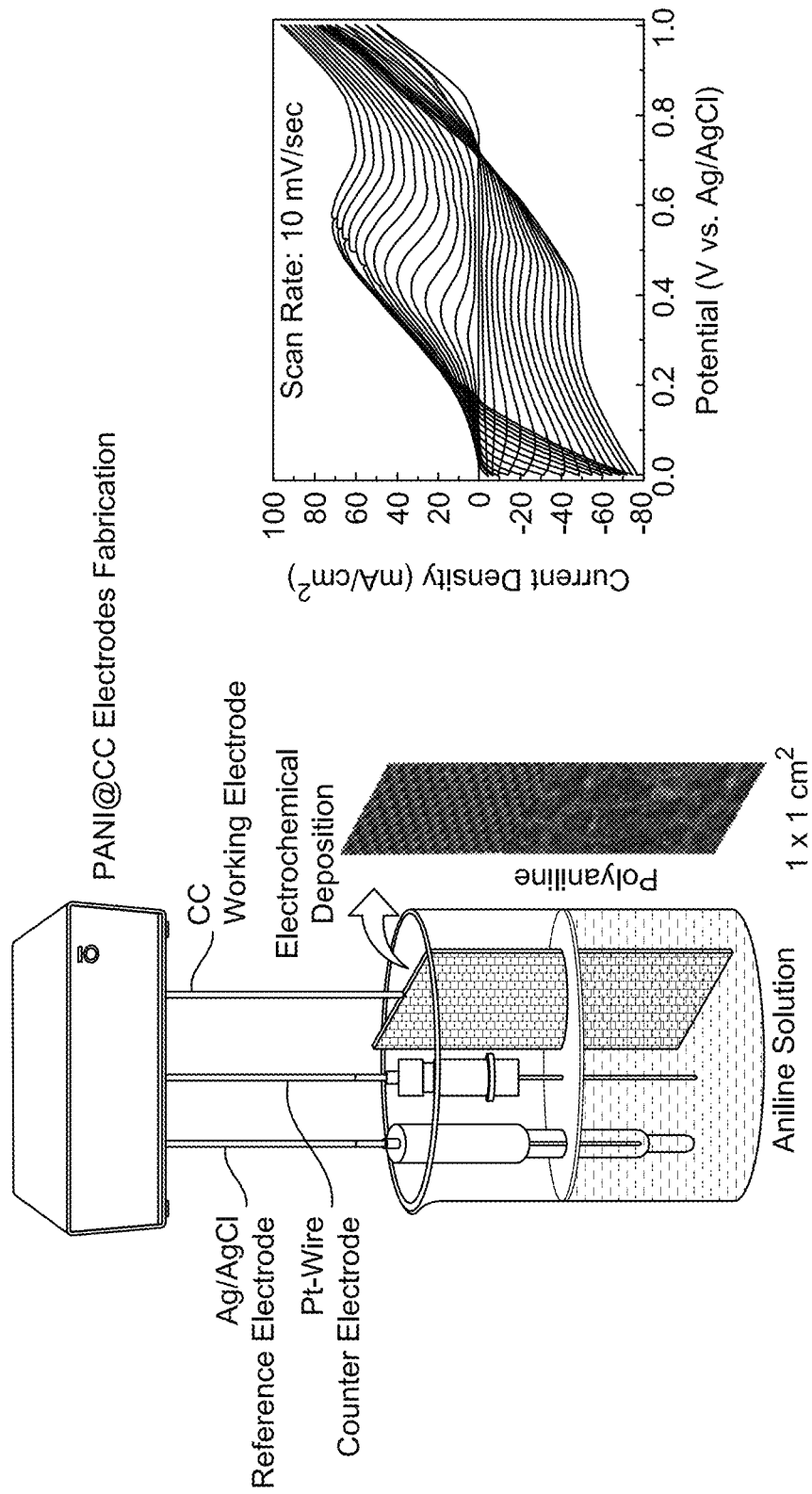
FIG. 1C is a schematic representation of fabrication of a positive supercapacitor electrode using polyaniline (PANI), according to an aspect of the present disclosure.

The following examples describe and demonstrate exemplary embodiments of the supercapacitor described herein. The examples are provided solely for the purpose of illustration and are not to be construed as limitations of the present disclosure, as many variations thereof are possible without departing from the spirit and scope of the present disclosure.
Materials Green tomato leaves were gathered from a garden in Dhahran, Saudi Arabia. Sodium bicarbonate ($NaHCO_3$), aniline, sulfuric acid ($H_2SO_4$), hydrochloric acid (HCl), 1-butyl-3-methylimidazolium hexafluorophosphate ($BMIM-PF_6$), 1-methyl-2-pyrrolidone (NMP) solvent, and polyvinylidene fluoride (PVDF, HSV900) binder were purchased from Sigma Aldrich (Sigma-Aldrich, St. Louis, Missouri, United States). All compounds were utilized in their obtained condition of purity. Carbon cloth (CC, HCP331-N) was obtained from AliExpress.com's Minihua store. High-purity nitrogen gas was provided by Specialty Gases Company Limited in Jubail, Kingdom of Saudi Arabia.
Tomato Leaves-Derived Hierarchical Porous Activated Carbon Network (TAC) Preparation Green tomato leaves 102 were gathered from a garden and dried to form naturally dried tomato leaves 104 (FIG. 1A). The dried tomato leaves 104 were rinsed with deionized (DI) water to eliminate any external contaminants before being dried in an electric oven at 100° C. for a period of 12 hours. After the cleaning, the dried tomato leaves 104 were pulverized in a kitchen grinder and were combined with sodium bicarbonate. The mixture was then heated in a tube furnace at 850° C. for five hours in a nitrogen atmosphere with a heating and cooling rate of 10° C. per minute and 5° C. per minute, respectively. The product that was obtained was washed with acid and DI water to eliminate any impurities, to obtain TAC. The impurities free product was dried at 80° C. for 12 hours. The activation process yields 10 to 20% by weight of the dried tomato leaves 104.
TAC on Carbon Cloth (CC)/TAC@CC Electrode Preparation FIG. 1B is a schematic representation of fabrication of the negative supercapacitor electrode using TAC. Electrodes made of TAC@CC were created using a straightforward drop-casting technique. To form the TAC@CC electrodes, 90% weight per weight (w/w.) of TAC in 1-methyl-2-pyrrolidinone (NMP) was combined with 10% w/w. of PVDF in NMP. An hour of ultrasonication was used to turn the resulting mixture into a uniform solution 106. The TAC@CC electrode was formed by dropping (as shown in FIG. 1B) the uniform solution 106 onto the CC (1 $cm^2$) and drying the CC in an electric oven at 80° C. for 12 hours.
Polyaniline (PANI) on Carbon Cloth/PANI@CC Electrode Fabrication FIG. 1C is a schematic representation of fabrication of a positive supercapacitor electrode using PANI. Electrodes made from PANI@CC were produced via an electrochemical deposition process. The PANI electrodeposition on CC was achieved using the capacitance-voltage profiling (CV) technique at 50 mV/sec scan rate in a solution of aniline (0.5 M) in $H_2SO_4$ (1.0 M). In a three-electrode system, the electrodeposition was performed using an operating potential window (OPW) between 0.0 V to 1.0 V vs. Ag/AgCl for 15 cycles. A working electrode, a reference electrode, and a counter electrode were made of CC, Ag/AgCl, and Pt wire, respectively. Shortly after the CV began, green layers of PANI began to form on the CC. The number of polymerization CV cycles was optimized, and 15 cycles were found to be optimal. After gently rinsing with DI water, the formed PANI@CC was allowed to dry at room temperature.
Symmetric and Asymmetric Supercapacitors Fabrication and Electrochemical Characterizations The fabricated TAC@CC electrodes were used as the positive electrode and the negative electrode to produce a TAC@symmetric supercapacitor. Similarly, the PANI@CC electrodes were used as the positive electrode and the negative electrode to produce a PANI@symmetric supercapacitor. The PANI@CC electrode was used as the positive electrode and the TAC@CC electrode was used as the negative electrode in the fabrication of an asymmetric supercapacitor. A normal laboratory filter paper was utilized as a separator which was soaked adequately in the ionic liquid electrolyte in both the symmetric and asymmetric supercapacitors.

A CHI-760E potentiostat (available at CH Instruments Inc., 3700 Tennison Hill Dr, Bee Cave, TX 78738, USA) was used to carry out electrochemical measurements such as CV, GCD (GCD graph is a Cayley graph over a finite abelian group defined by greatest common divisors), and electrochemical impedance spectroscopy (EIS) on the fabricated symmetric supercapacitors and the asymmetric supercapacitor. An areal capacitance of the fabricated supercapacitors was measured from the cyclic voltammograms by applying the below equation:

$$C = \frac{\int I \times dV}{A \times v \times \Delta V}, \quad (1)$$

where, the areal capacitance (C) is measured in F/cm², ∫I×dV provides an area exhibited by the cyclic voltammogram in watts, a working area of two electrodes in cm² is represented by A, the scan rate in volts per second is shown by v, and the applied OPW in volts is represented by ΔV. Similarly, the areal capacitance from GCD measurements was using the below equation:

$$C = \frac{I \times t}{A \times \Delta V}, \quad (2)$$

where, the areal capacitance (C) is measured in F/cm², I is a constant charging and discharging current measured in amperes, the working area of two electrodes in cm² is represented by A, t is the discharging time in seconds, and the applied OPW in volt is represented by ΔV.

The energy density (E with units Wh/cm²) and power density (P with units W/cm²) of the supercapacitor are measured performance parameters which were calculated using equations (3) and (4), respectively.

$$E = 0.5 \times \frac{C \times \Delta V^2}{3600} \times 1000. \quad (3)$$

$$P = \frac{E}{t} \times 3600. \quad (4)$$

High-resolution field-emission-scanning-electron-microscopy (FESEM) (TESCAN-LYRA-3, Czech Republic) was used to investigate the morphology of the fabricated electrodes. Elemental analysis of the fabricated materials was carried out by using energy-dispersive X-ray spectroscopy (EDS) detector equipped with field emission scanning electron microscopy (FESEM). A transmission electron microscope (TEM: JEOL, JEM 2100F, available at Jeol USA Inc., Pleasanton, USA) was also used to obtain morphological and diffraction properties of the TAC. X-ray diffraction (XRD) analysis was used to investigate the TAC's phase purity and crystallographic structure using a Rigaku Miniflex-II diffractometer (available at Applied Rigaku Technologies, Inc., Austin, Texas, USA) with Cu—K-Alpha radiations (%=0.15416 nm) working at a constant voltage (40 kV) and a constant current (30 mA). At room temperature, the graphitic or defective structure of the TAC was determined and investigated using a Raman spectrometer (iHR320 HORIBA, 2, Miyanohigashi-cho, Kisshoin, Minami-Ku, Kyoto, 601-8510, Japan) with a green (300 mW, 532 nm) laser and equipped with a charge-coupled device detector. The pore size distribution and specific surface area (SSA) of the TAC were investigated using a SSA and porosity analyzer (ASAP 2020, Micromeritics) and a nitrogen adsorption desorption Brunauer-Emmett-Teller (BET) method.

Figure 2A:
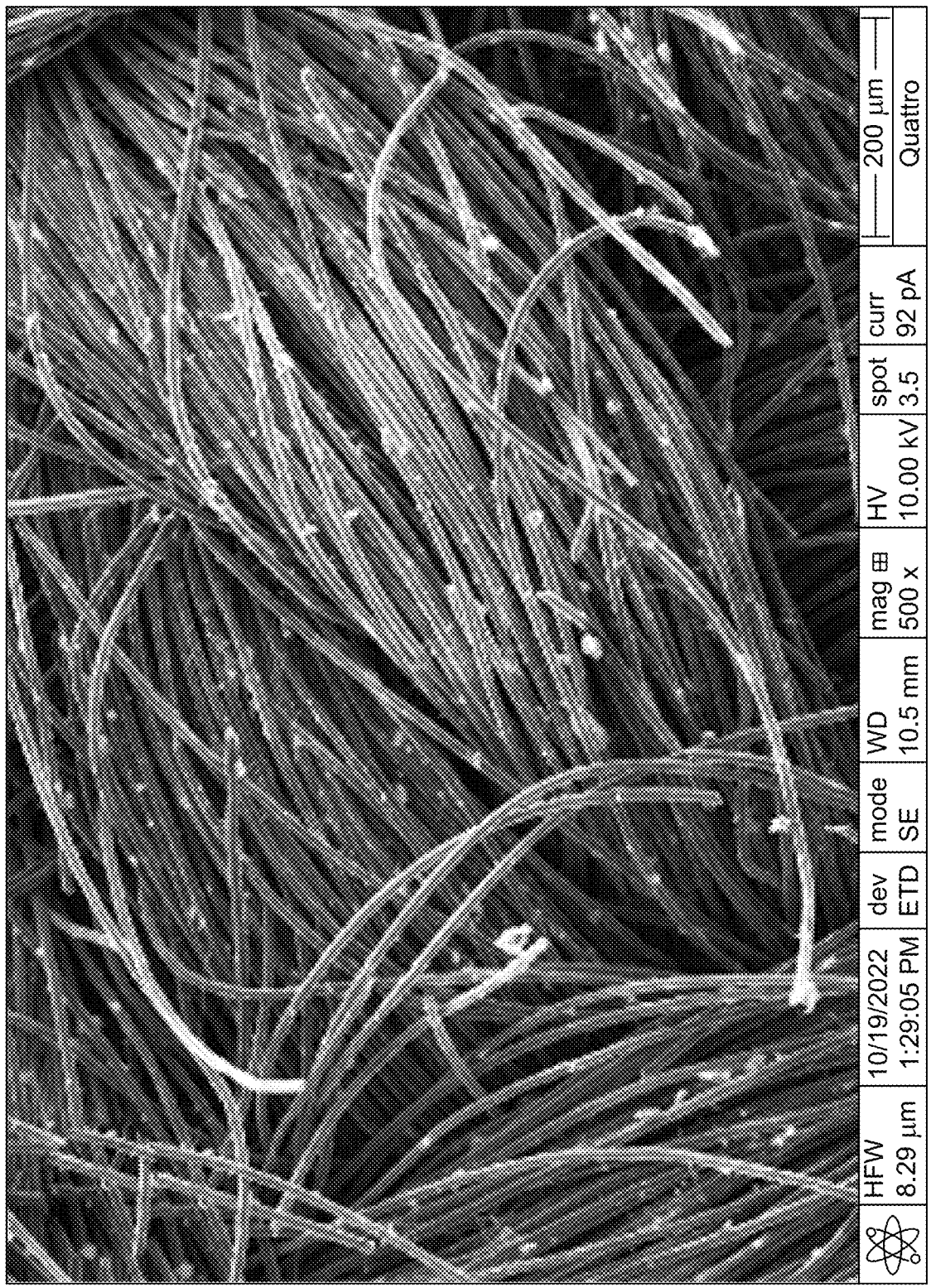
FIG. 2A is a field-emission-scanning-electron-microscopy (FESEM) micrograph of bare carbon cloth (CC) at 500× magnification, according to an aspect of the present disclosure.
Figure 2B:
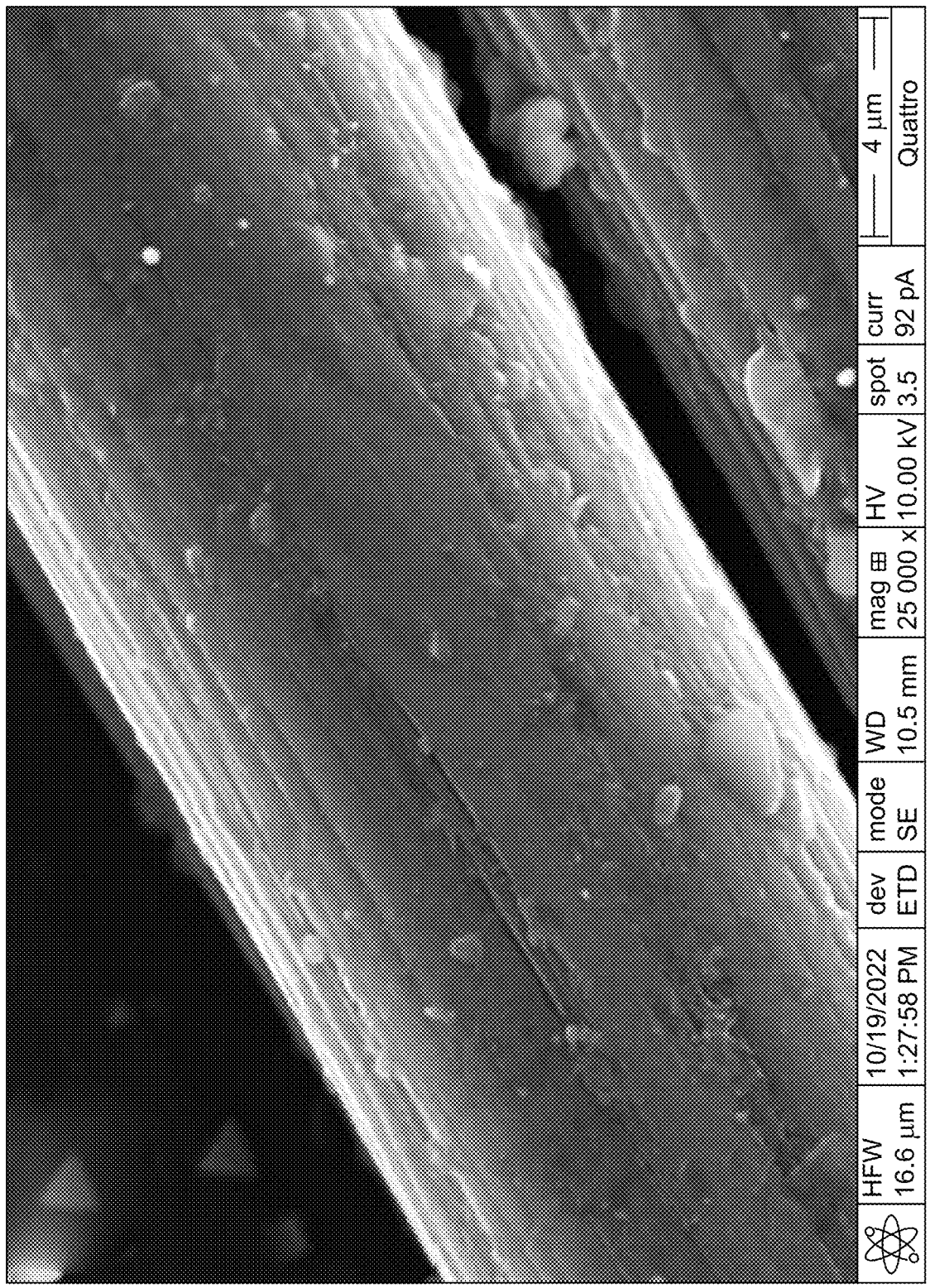
FIG. 2B is the FESEM micrograph of the bare carbon cloth (CC) at 25000× magnification, according to an aspect of the present disclosure.
Figure 2C:
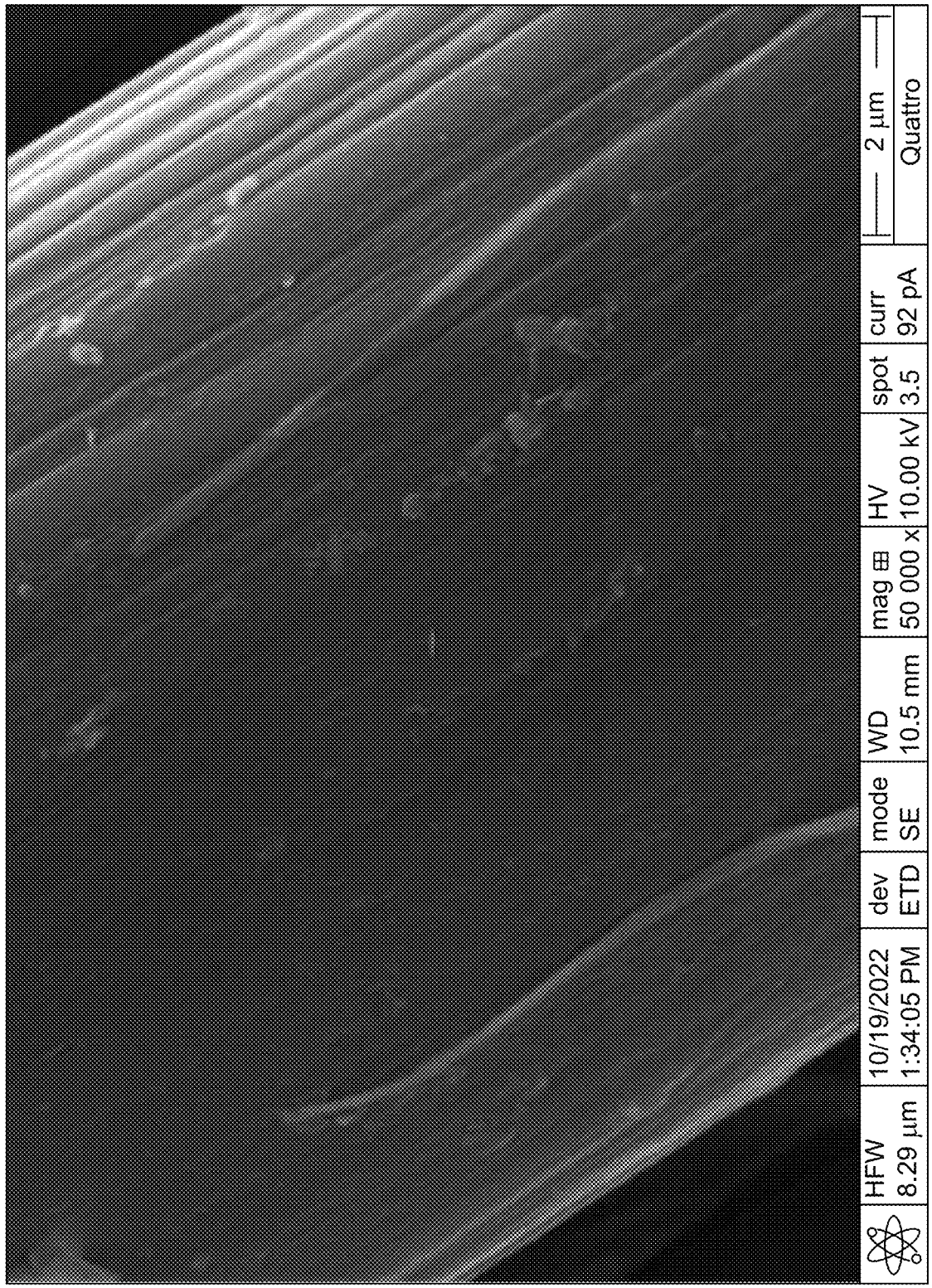
FIG. 2C is the FESEM micrograph of the bare carbon cloth (CC) at 50000× magnification, according to an aspect of the present disclosure.
Figure 2D:
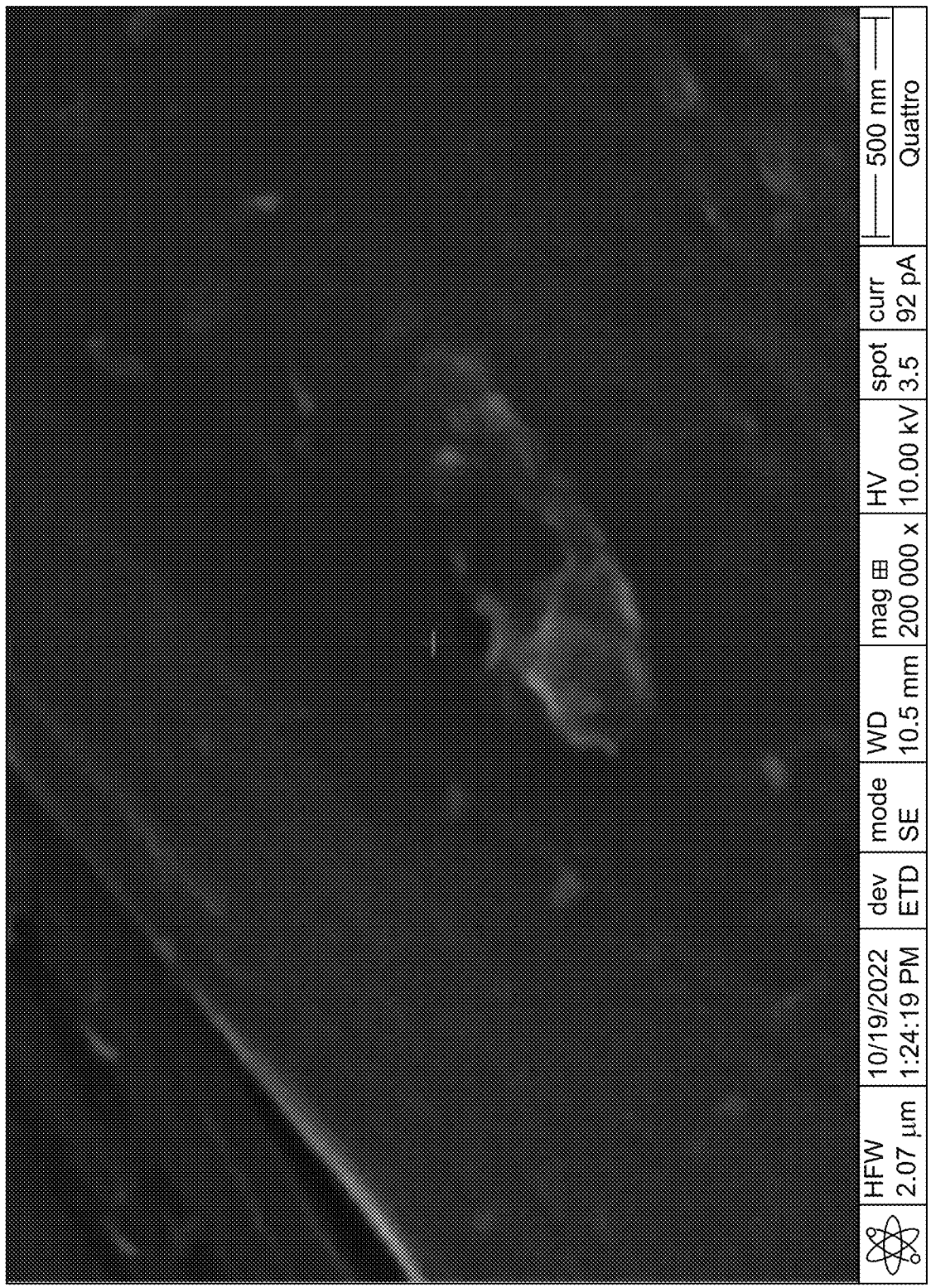
FIG. 2D is the FESEM micrograph of the bare carbon cloth (CC) at 200000× magnification, according to an aspect of the present disclosure.
Figure 2E:
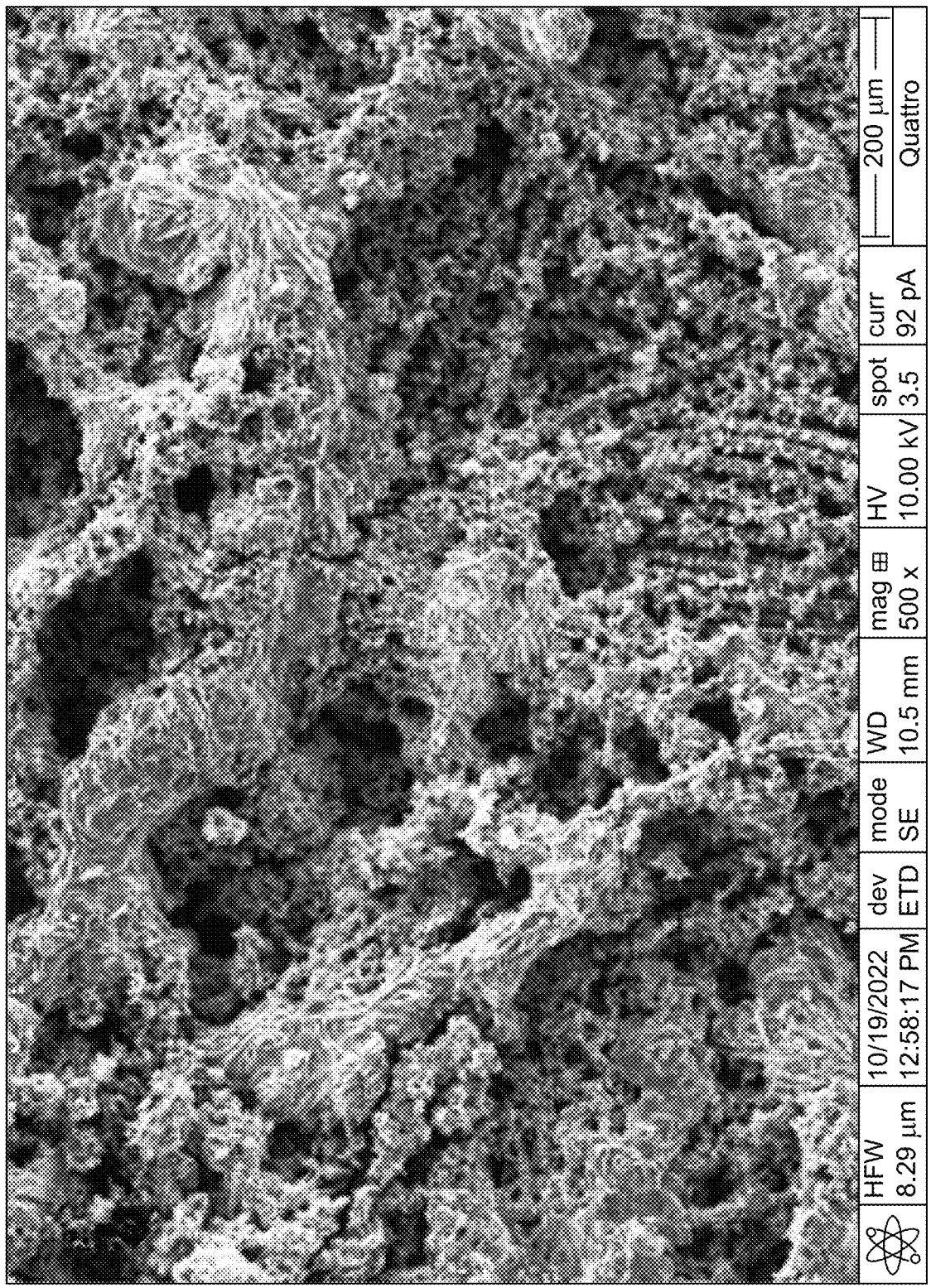
FIG. 2E is a FESEM micrograph of electrochemically deposited PANI on CC (PANI@CC) at 500× magnification, according to an aspect of the present disclosure.
Figure 2F:
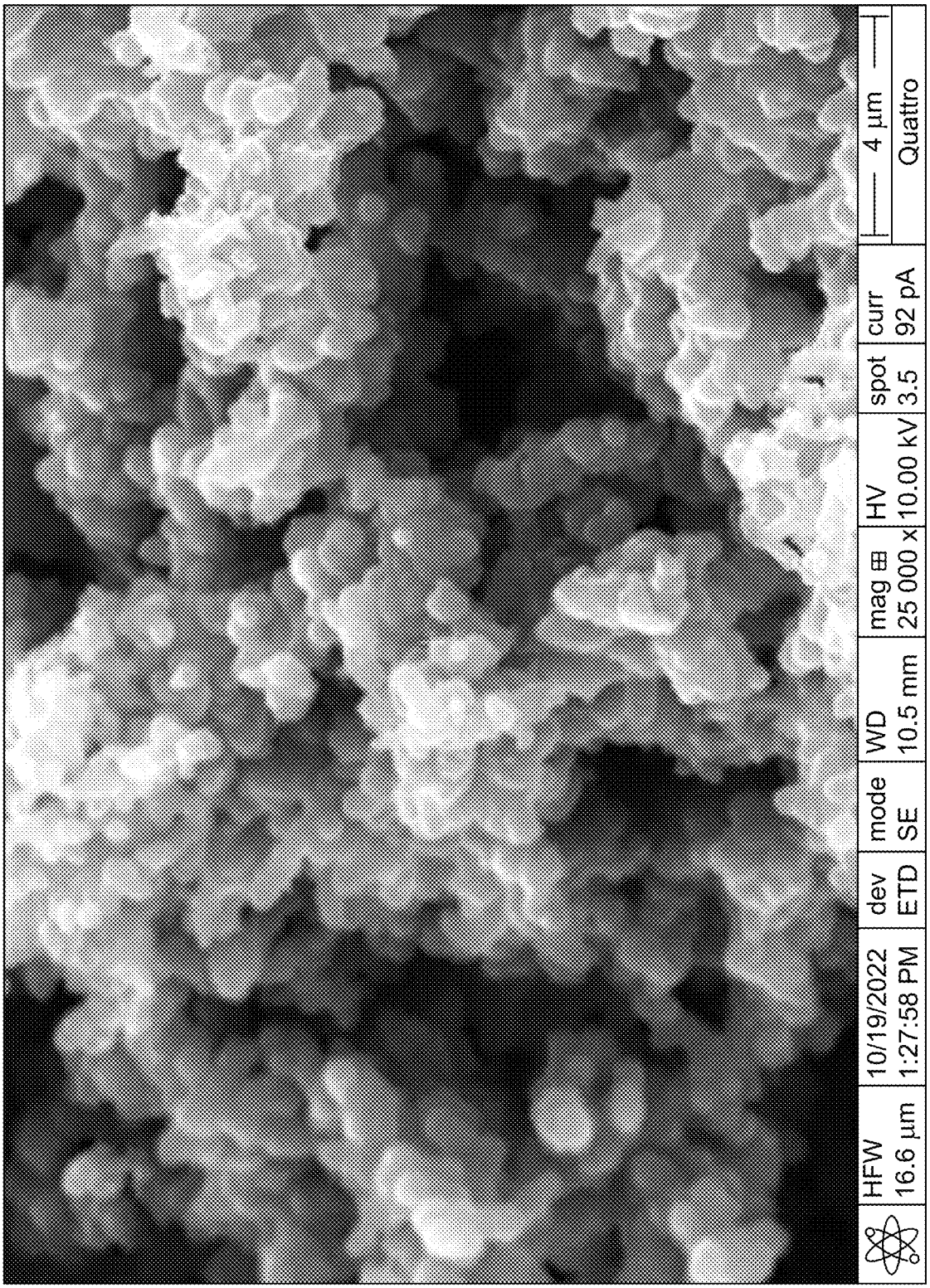
FIG. 2F is the FESEM micrograph of PANI@CC at 25000× magnification, according to an aspect of the present disclosure.
Figure 2G:
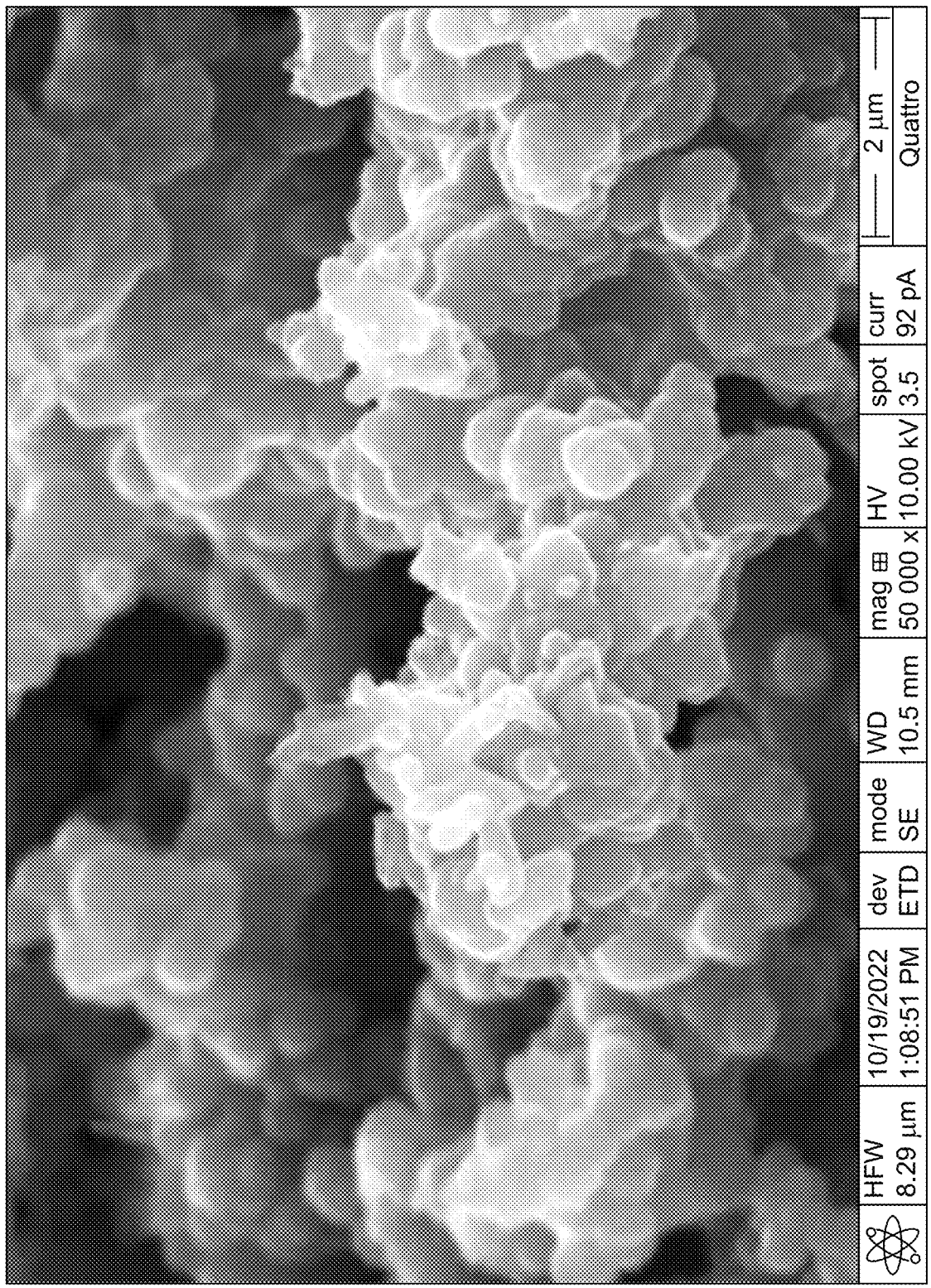
FIG. 2G is the FESEM micrograph of PANI@CC at 50000× magnification, according to an aspect of the present disclosure.
Figure 2H:
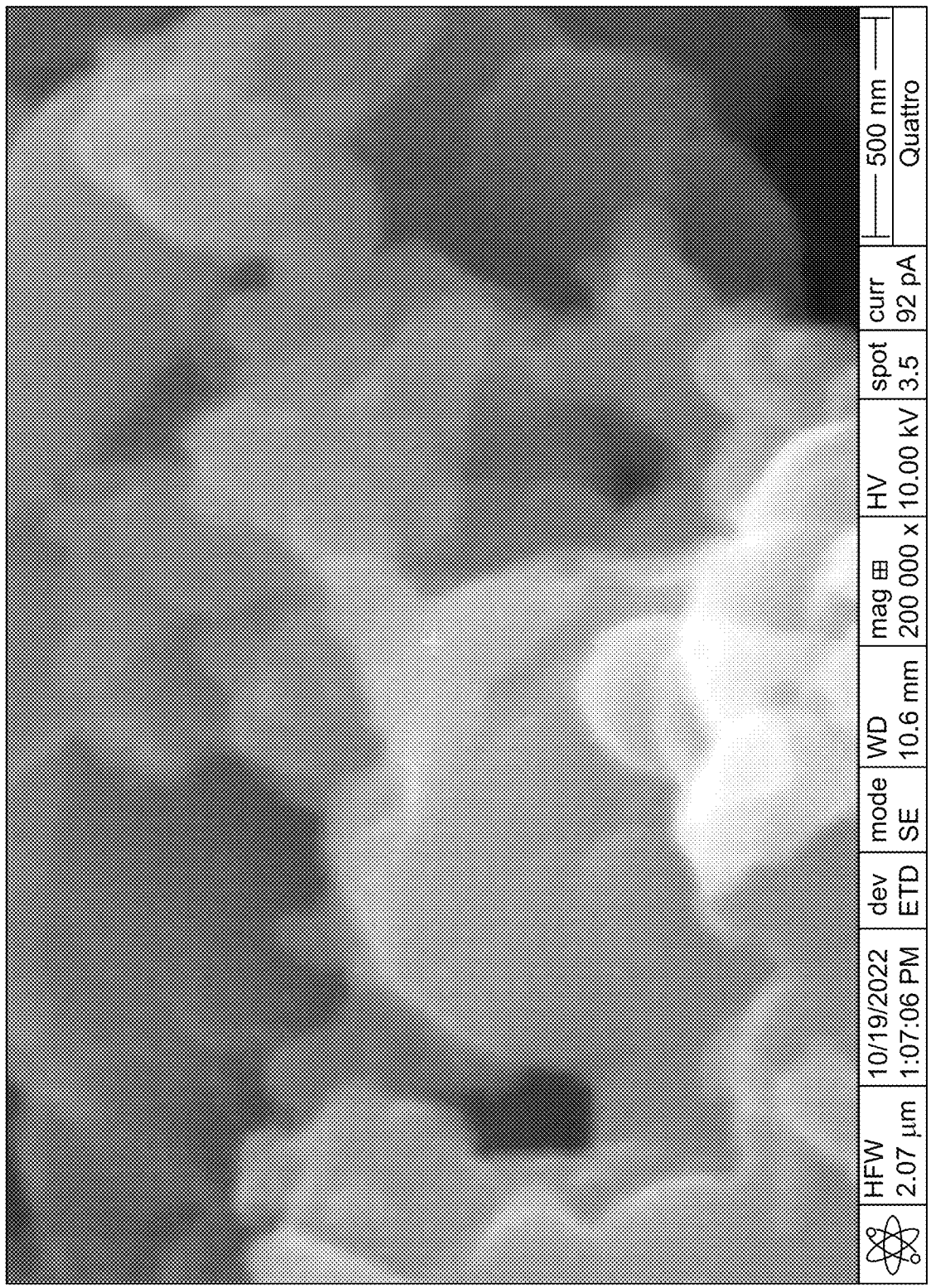
FIG. 2H is the FESEM micrograph of PANI@CC at 200000× magnification, according to an aspect of the present disclosure.
Figure 21:
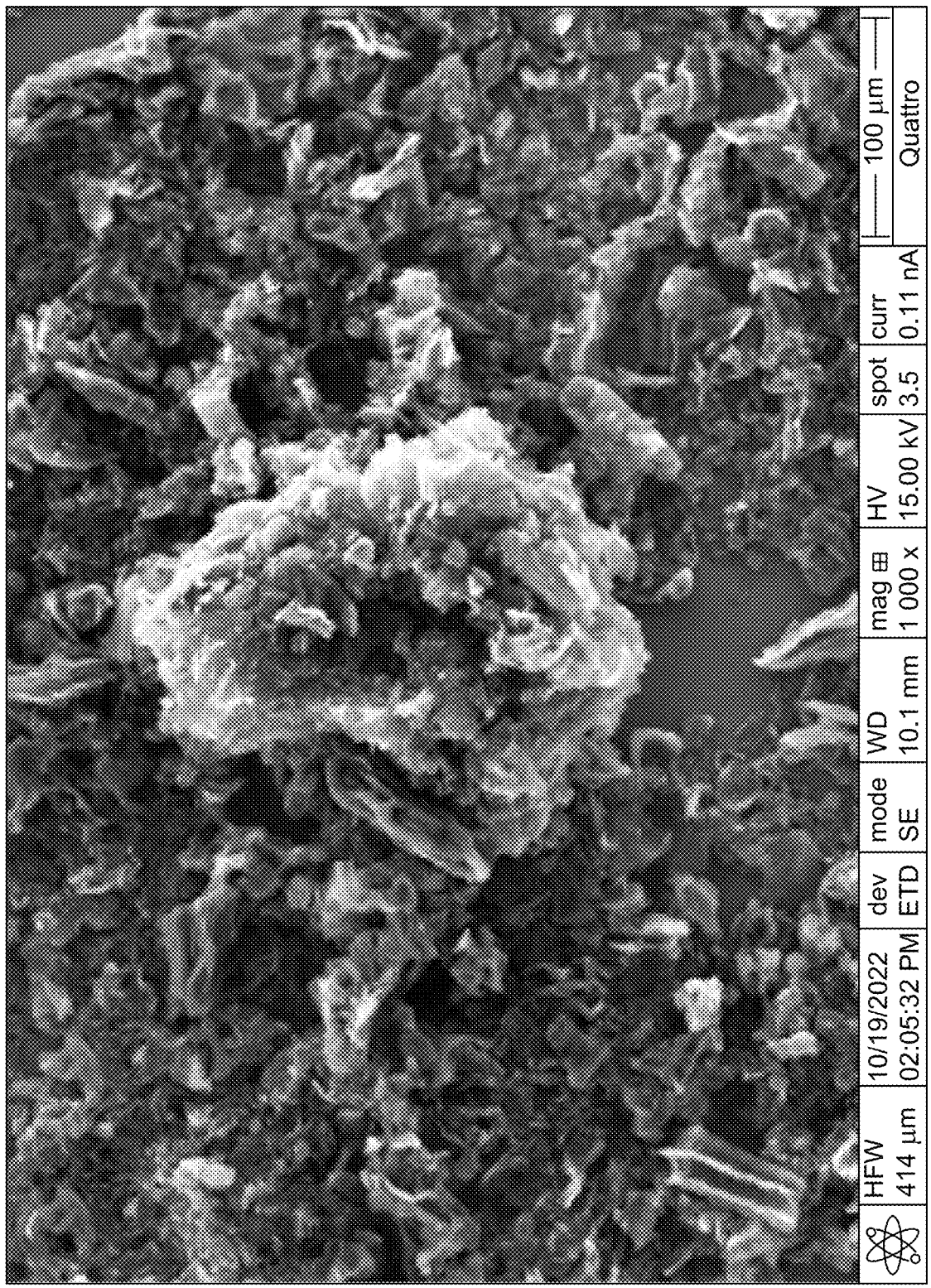
Figure 2J:
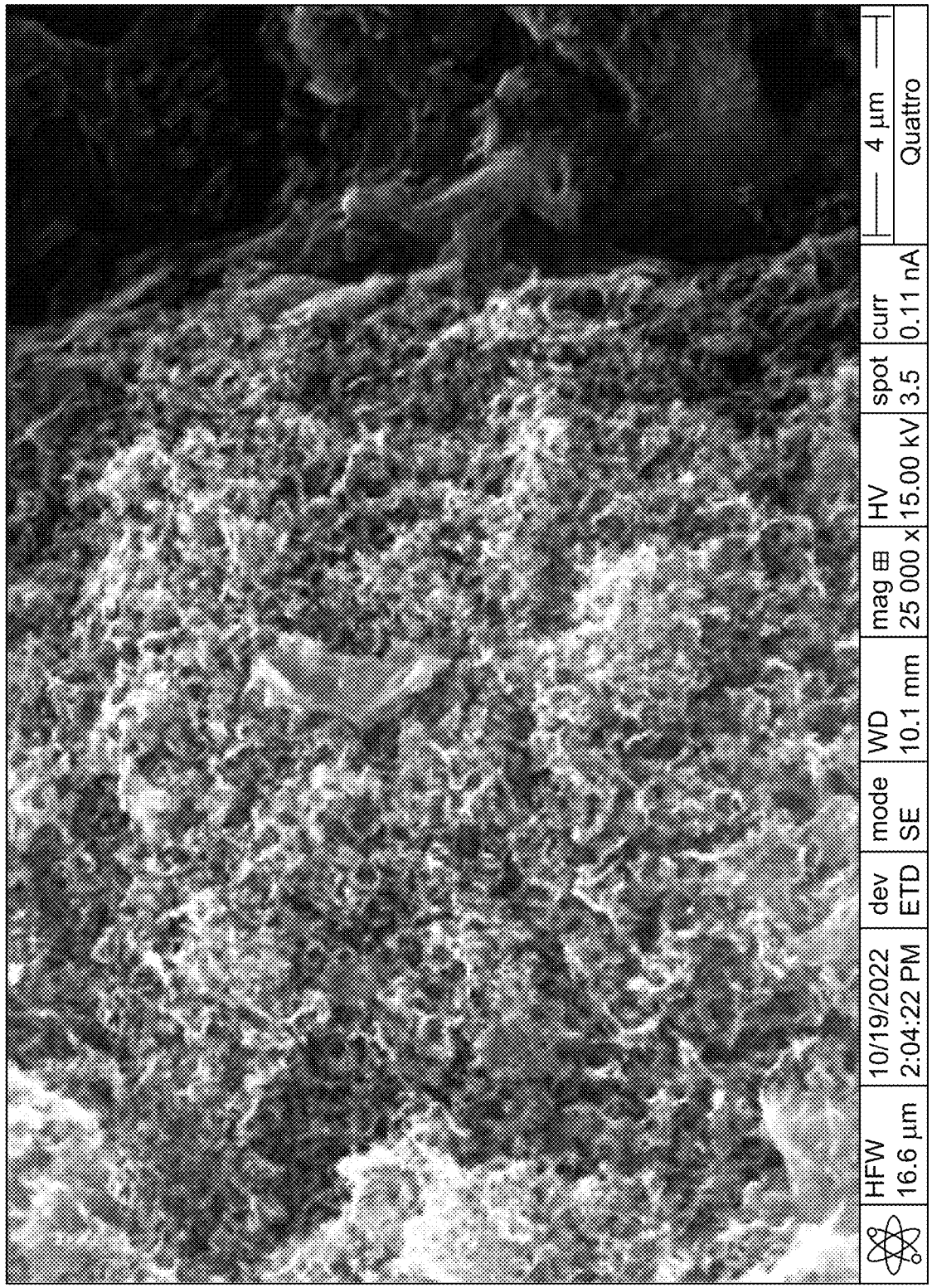
FIG. 2J is the FESEM micrograph of TAC@CC at 25000× magnification, according to an aspect of the present disclosure.
Figure 2K:
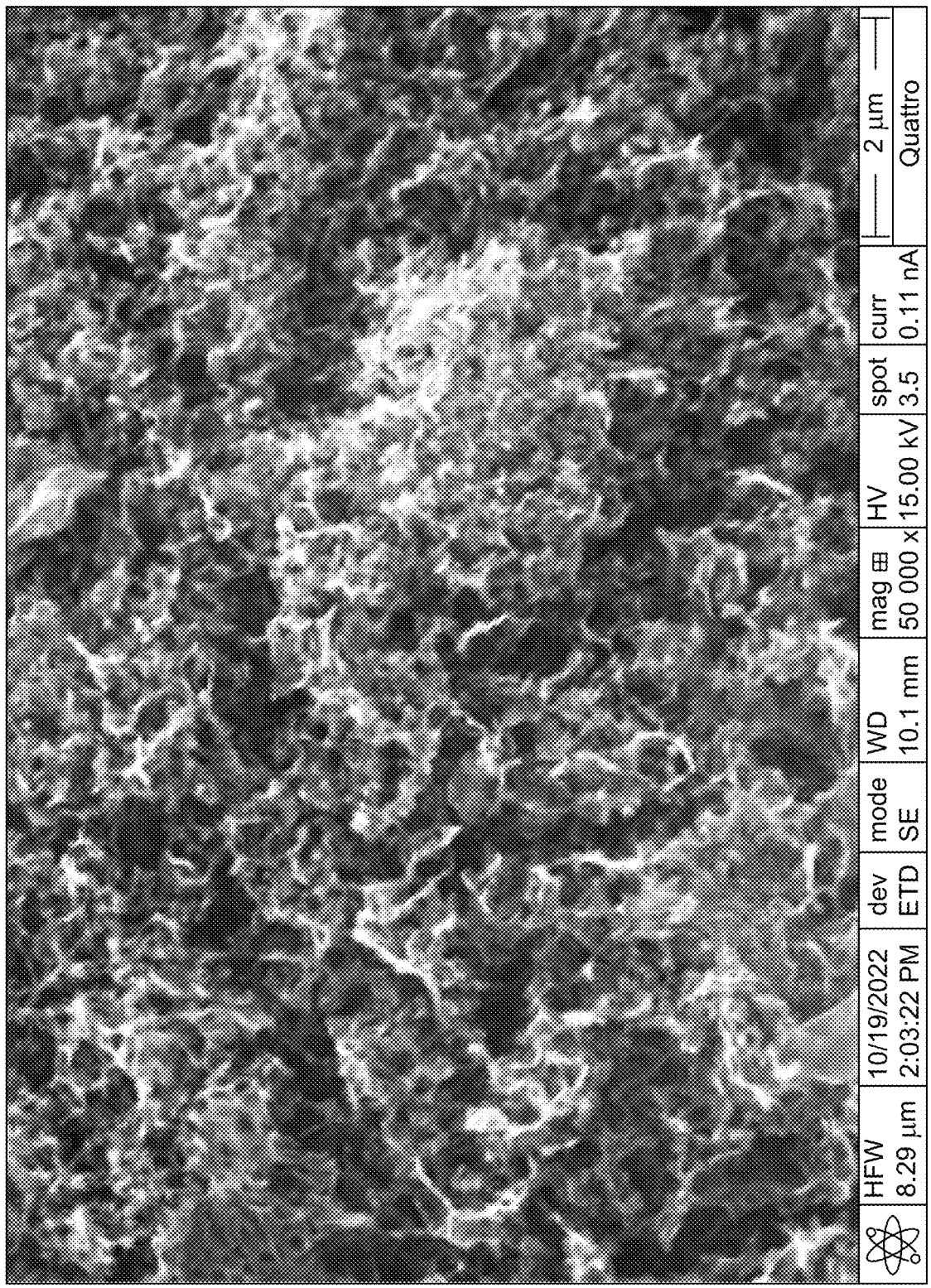
FIG. 2K is the FESEM micrograph of TAC@CC at 50000× magnification, according to an aspect of the present disclosure.
Figure 2L:
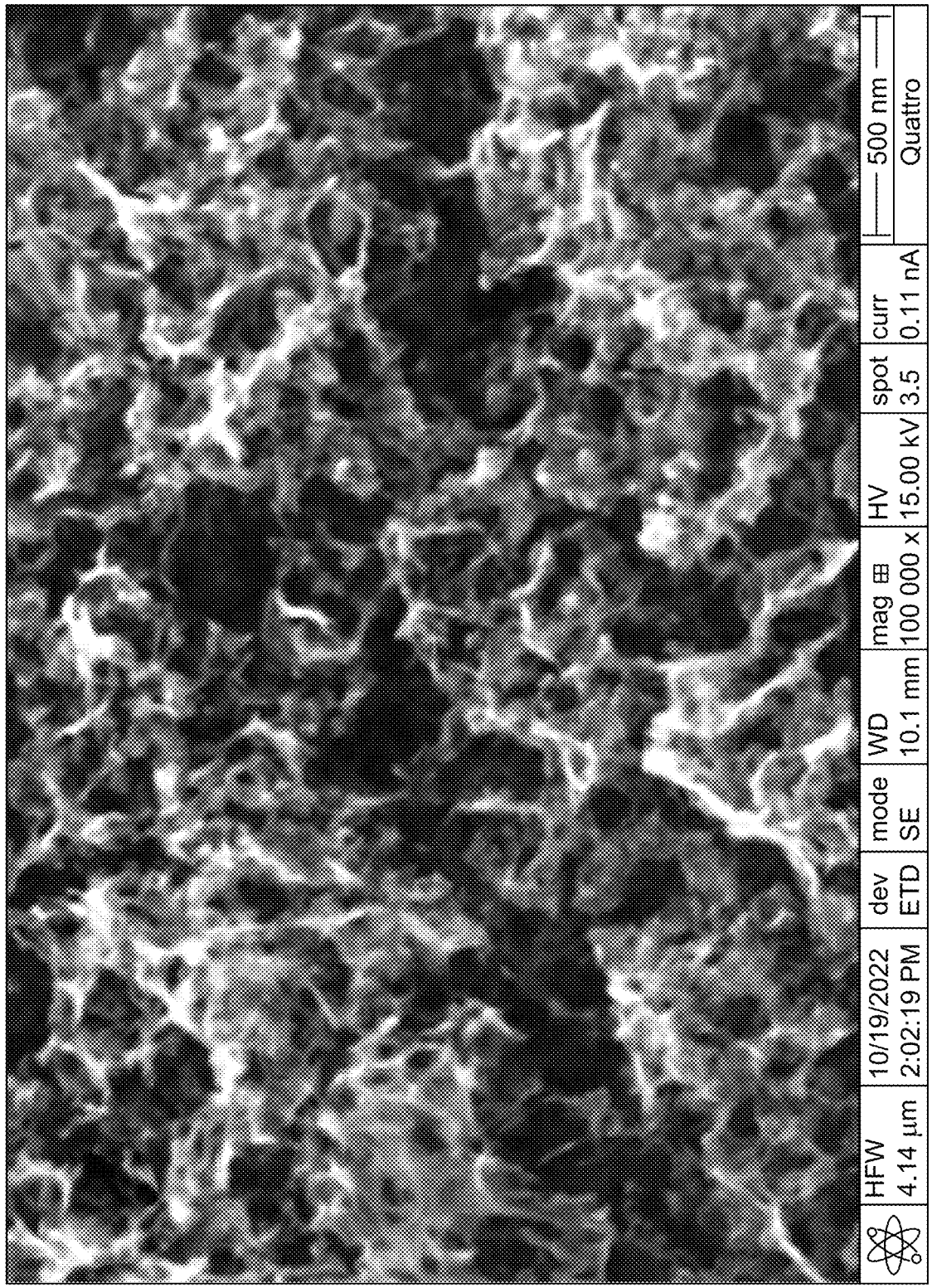
FIG. 2L is the FESEM micrograph of TAC@CC at 100000× magnification, according to an aspect of the present disclosure.

The FESEM was used to characterize the microstructure of the CC before and after the PANI and TAC deposition processes. The surface of bare CC was a smooth fiber type, as shown in FIG. 2A to FIG. 2D, with an average diameter of about 5 µm. After 15 cycles of CV electrochemical PANI deposition, the CC surface became rough and decorated with nanoparticles (see FIG. 2E to FIG. 2H), revealing a uniform distribution of PANI nanoparticles on each CC fiber. A clear structure was observed in a high FESEM magnification of PANI@CC (see FIG. 2G and FIG. 2H) that was built up from PANI nanoparticles with an average diameter of about 0.2 µm. It may be noticed that PANI nanoparticles are distributed uniformly on the CC and are connected to nearby CC via void spaces. This structure may be ideal for electrolyte ion absorptions. The void spaces may be porous and allow for movement of electrolytes to and from the positive electrode. The PANI nanoparticles may be 0.01 to 10 µm, preferably 0.1 to 5 µm, more preferably 0.1 to 1 µm, and yet more preferably about 0.2 µm in diameter. The void spaces may be 0.1 to 1000 µm, preferably 1 to 800 µm, and more preferably, 5 to 500 µm in diameter. The FESEM images of the drop-cast TAC over CC (TAC@CC), shown in FIG. 2I to FIG. 2L, demonstrate the nanosheet type morphology of the prepared TAC. FIG. 2I depicts an FESEM micrograph of the TAC@CC at low magnification, revealing that the CC is wholly covered with TAC nanosheets. The morphology of their nanosheets is depicted in the magnified FESEM image (FIG. 2J to FIG. 2L). Such nanosheet-type morphology may allow for the penetration of electrolyte ions and enhanced supercapacitor electrochemical performance.

Figure 3A:
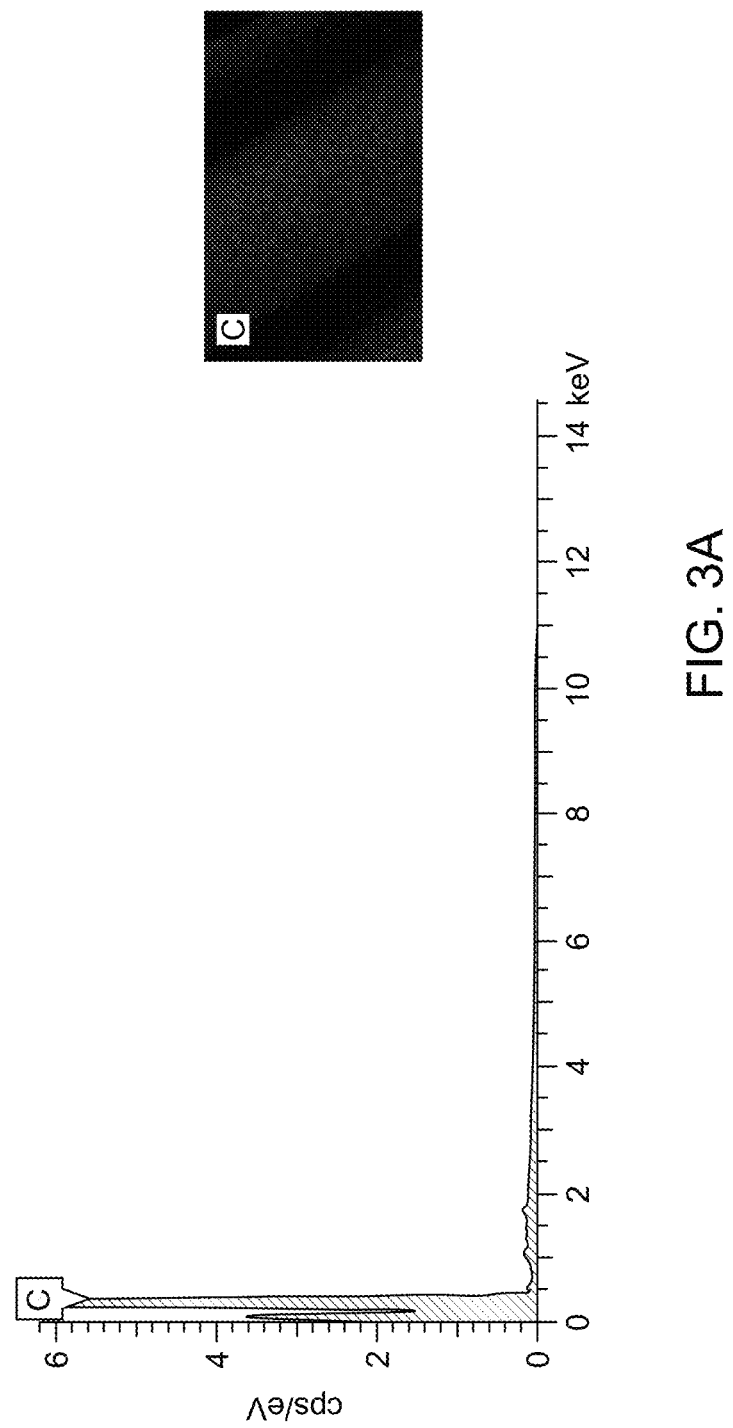
FIG. 3A is energy-dispersive X-ray spectroscopy (EDS) of the bare CC and corresponding elemental mapping, according to an aspect of the present disclosure.
Figure 3B:
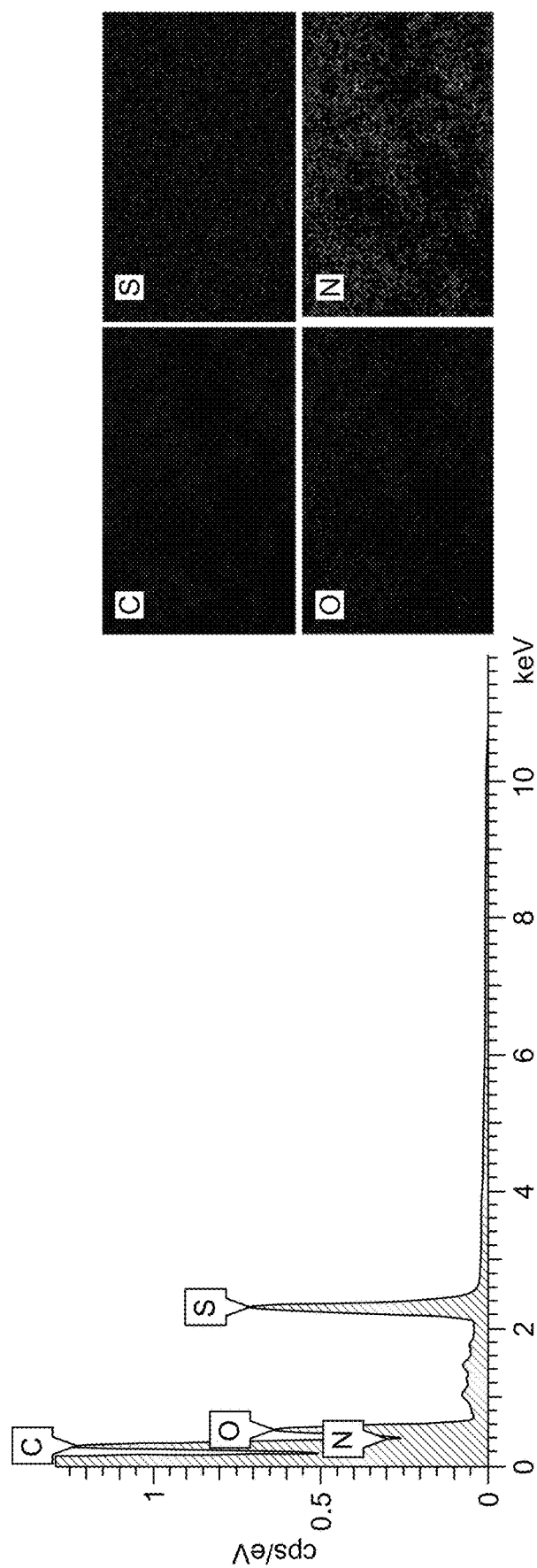
FIG. 3B is EDS of PANI@CC and corresponding elemental mapping, according to an aspect of the present disclosure.
Figure 3C:
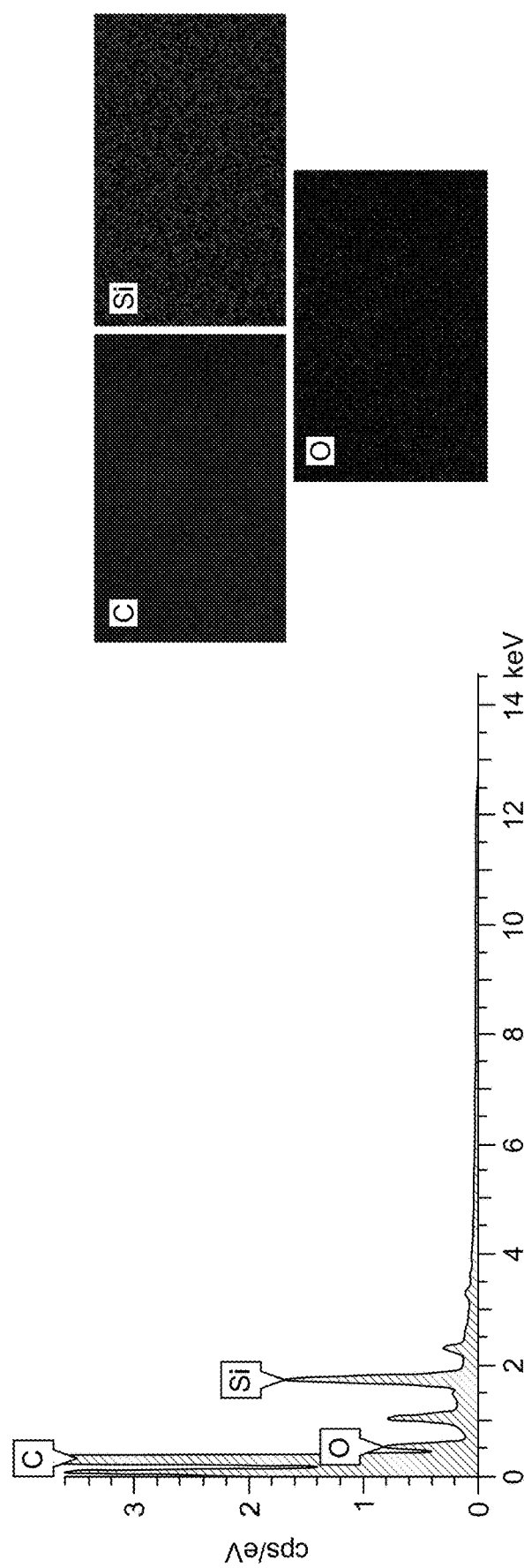
FIG. 3C is EDS of TAC@CC and corresponding elemental mapping, according to an aspect of the present disclosure.

The elemental analysis and mapping of the electrode materials was done using an EDS technique. As shown in FIG. 3A, EDS spectrum and a corresponding elemental mapping represent that the bare CC exhibited carbon as the only element without any impurity. The EDS spectrum of PANI@CC is shown in FIG. 3B, with the respective peaks corresponding to the detected elements of carbon, nitrogen, oxygen, and sulfur. The sulfur and oxygen peaks are due to sulfate ion incorporation during PANI electrochemical deposition in the $H_2SO_4$ acid electrolyte bath. No additional elements were found, indicating that there were no impurities in the prepared PANI@CC. The corresponding elemental mapping images show the uniform spatial distribution of the elements (C, S, O, and N) present in the PANI@ CC. Similarly, the EDS spectrum of the TAC@CC, in FIG. 3C, shows carbon as the major element with minor elements as oxygen and silicon. Silicon may be found in the tomato leaves, whereas oxygen may be present in activated carbon. The elemental mapping images for the TAC@CC showed that the C and O elements are uniformly distributed across the surface of the TAC nanosheets.

Figure 4A:
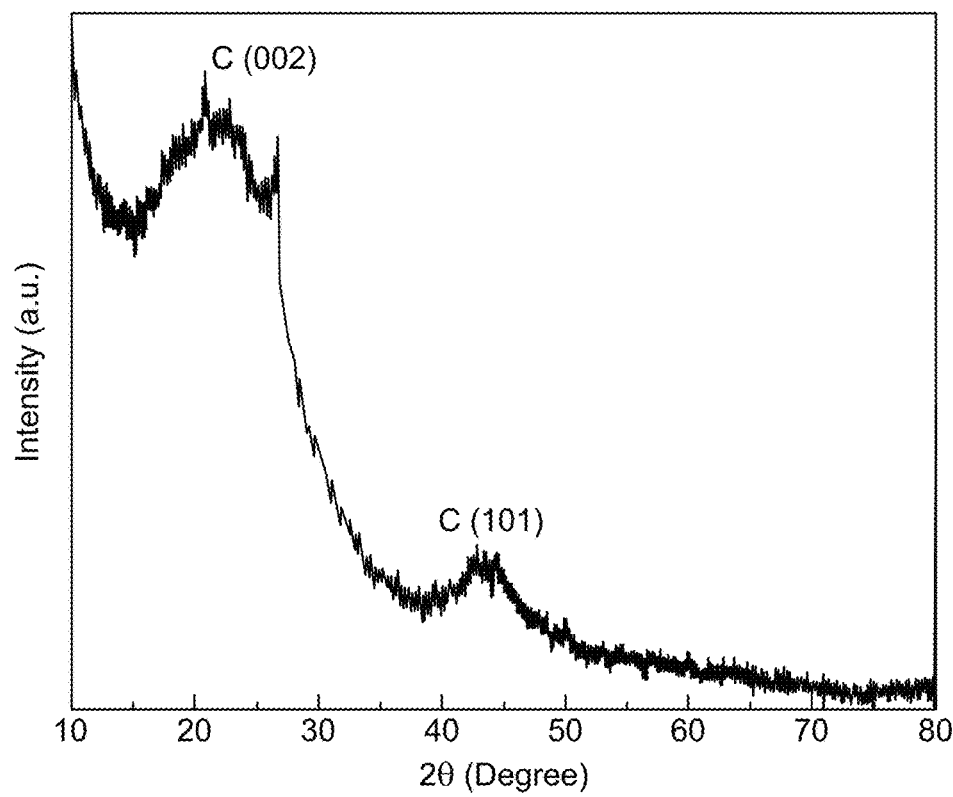
FIG. 4A is an X-ray diffraction (XRD) pattern of TAC, according to an aspect of the present disclosure.
Figure 4B:
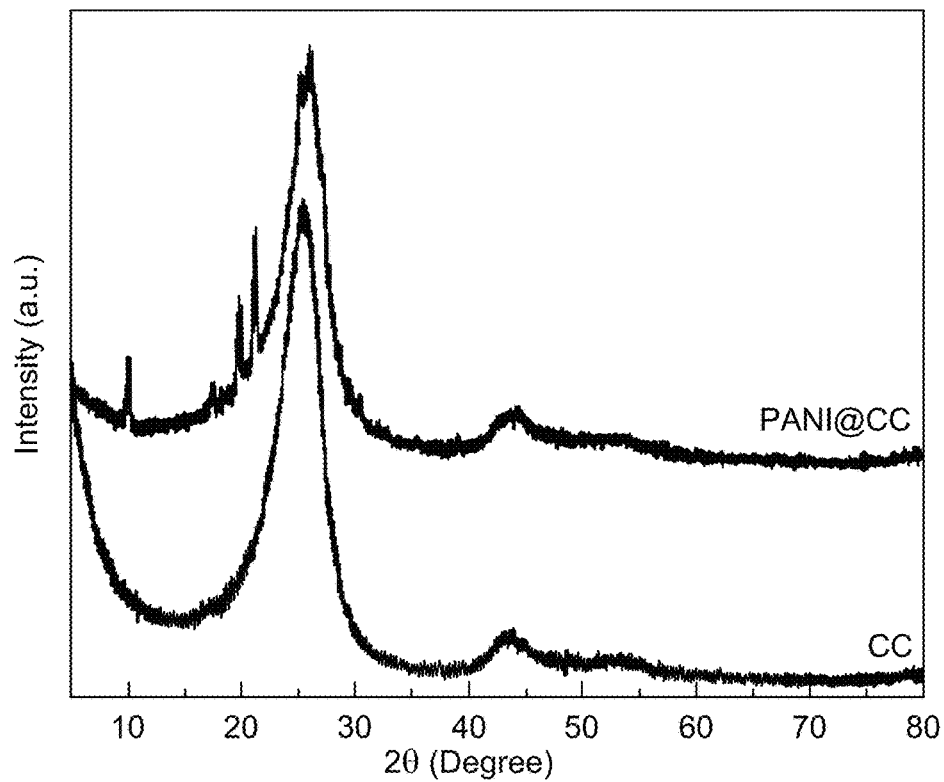
FIG. 4B is an XRD pattern of CC and PANI@CC, according to an aspect of the present disclosure.

The diffraction nature and phase formation of the prepared TAC were investigated using XRD. FIG. 4A depicts the TAC XRD patterns with a pure graphitic carbon signature. The TAC XRD spectrum shows two peaks. The first characteristic broad peak at about 2θ=25° is assigned to C(002) diffraction peak, which accounts for graphitic carbon reflection. The second, less intense, peak at about 2θ=43° is assigned to C(101) diffraction peak, which accounts for amorphous carbon. FIG. 4B depicts the CC and PANI@CC XRD patterns. Similar peaks are shown in CC and PANI@CC spectra as in the TAC XRD spectrum (See FIG. 4A).

Figure 4C:
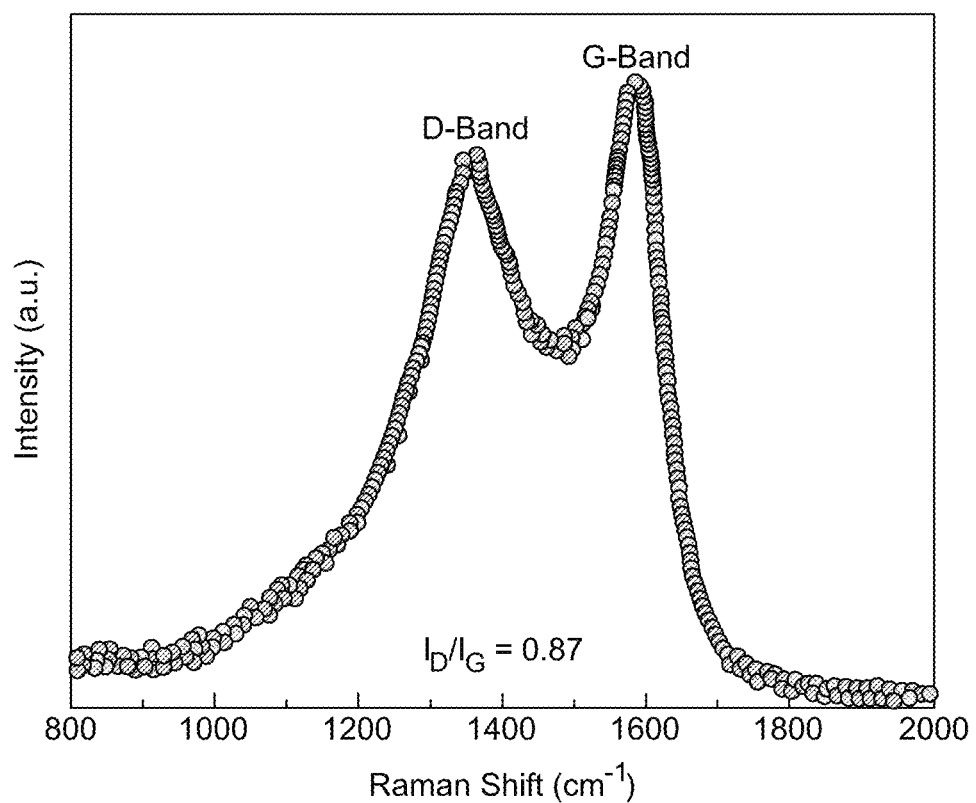
FIG. 4C is a Raman spectroscopy spectrum of TAC, according to an aspect of the present disclosure.

As shown in FIG. 4C, the TAC's Raman spectroscopy spectrum includes two peaks. A disordered band (D-band) and a graphitic band (G-band). The number of defects in the structure is represented by a ratio of integrated D-band and G-band intensities (i.e., $I_D/I_G$). The TAC's calculated $I_D/I_G$ ratio is 0.87, indicating a greater concentration of graphitic carbon (i.e., ordered carbon) over disordered carbon.

Figure 5A:
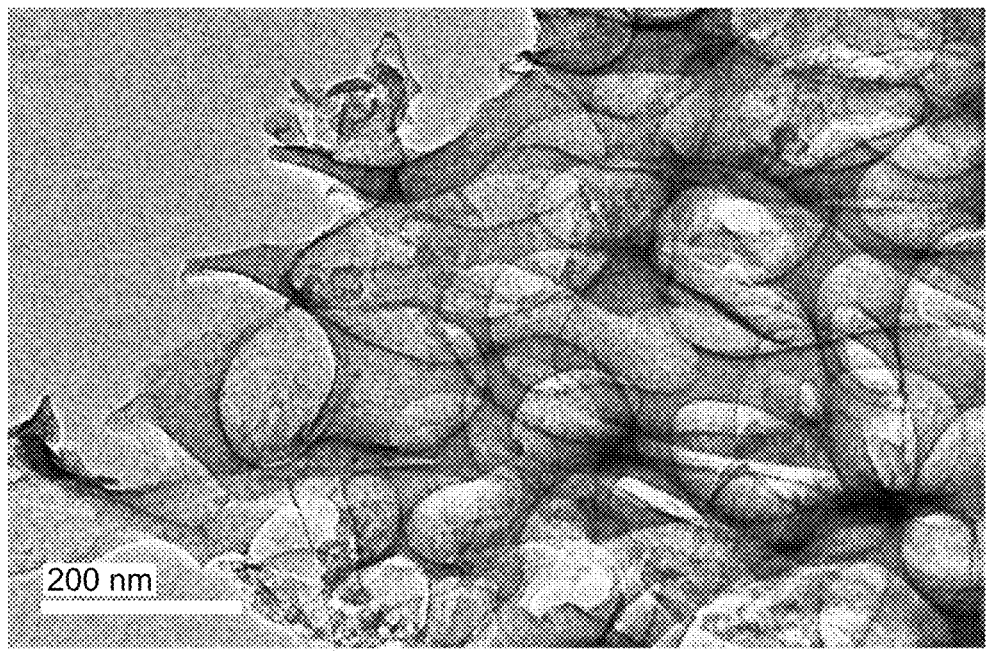
FIG. 5A is a transmission electron microscope (TEM) image of TAC at a scale of 200 nm, according to an aspect of the present disclosure.
Figure 5B:
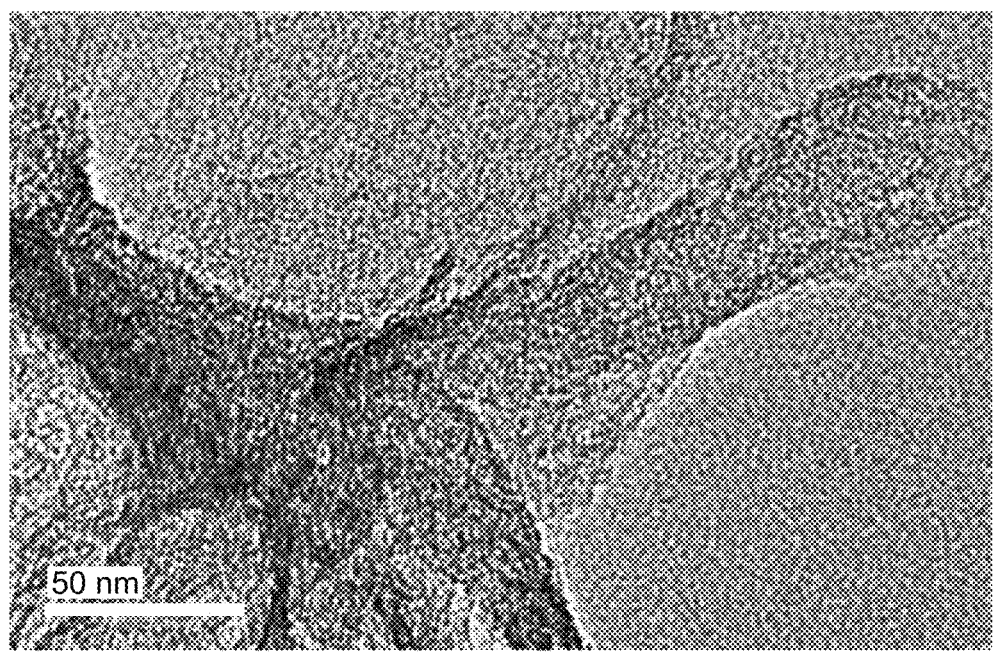
FIG. 5B is another transmission electron microscope (TEM) image of TAC at a scale of 50 nm, according to an aspect of the present disclosure.
Figure 5C:
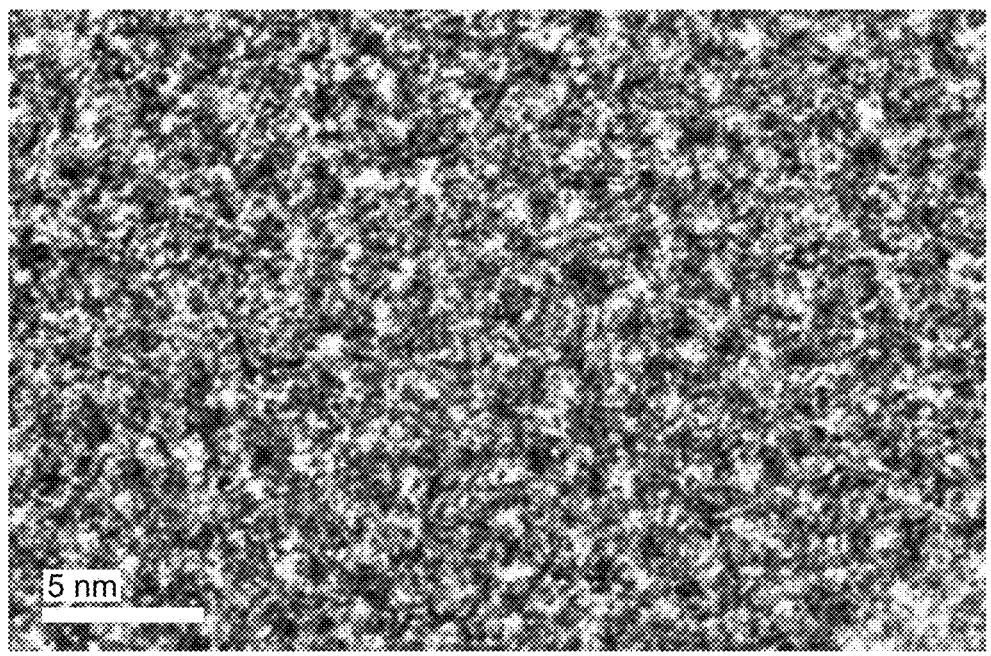
FIG. 5C is a high-resolution transmission electron microscope (HRTEM) image of TAC at a scale of 5 nm, according to an aspect of the present disclosure.
Figure 5D:
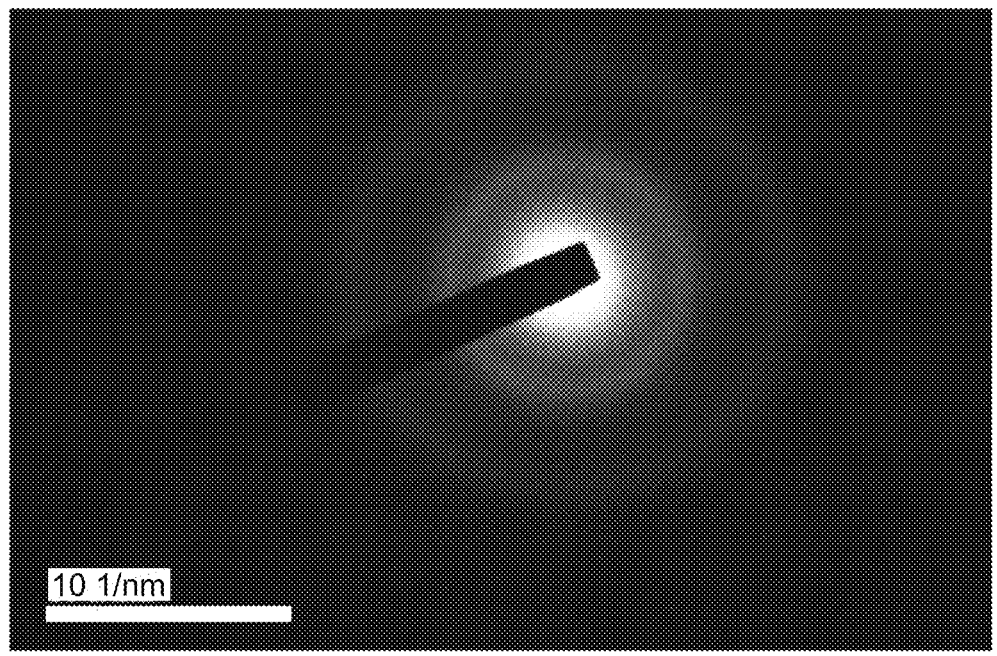
FIG. 5D is a selected area electron diffraction (SAED) pattern of TAC, according to an aspect of the present disclosure.

Transmission electron microscopy (TEM) was also used to examine the morphology of the TAC. FIG. 5A and FIG. 5B indicates that the TAC primarily includes ultrathin and well-dispersed nanosheets. The related high-resolution transmission electron microscopy (HRTEM) image (FIG. 5C) and selected area electron diffraction (SAED) pattern (FIG. 5D) showed no atomic ordering (no atomic fringes in HRTEM) or clear sharp diffraction rings. This indicates the semi-graphitic nature of the prepared TAC, which is supported by the XRD data.

Figure 6A:
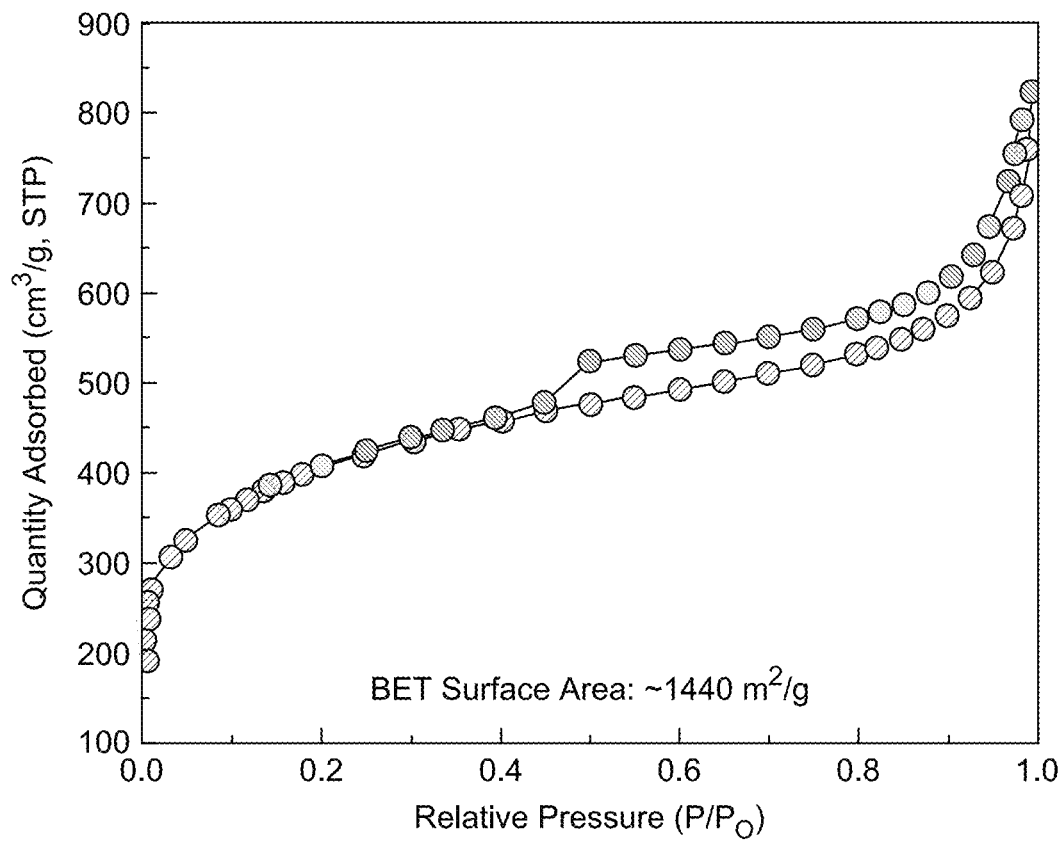
FIG. 6A is a nitrogen adsorption/desorption isotherm curve of the TAC, according to an aspect of the present disclosure.
Figure 6B:
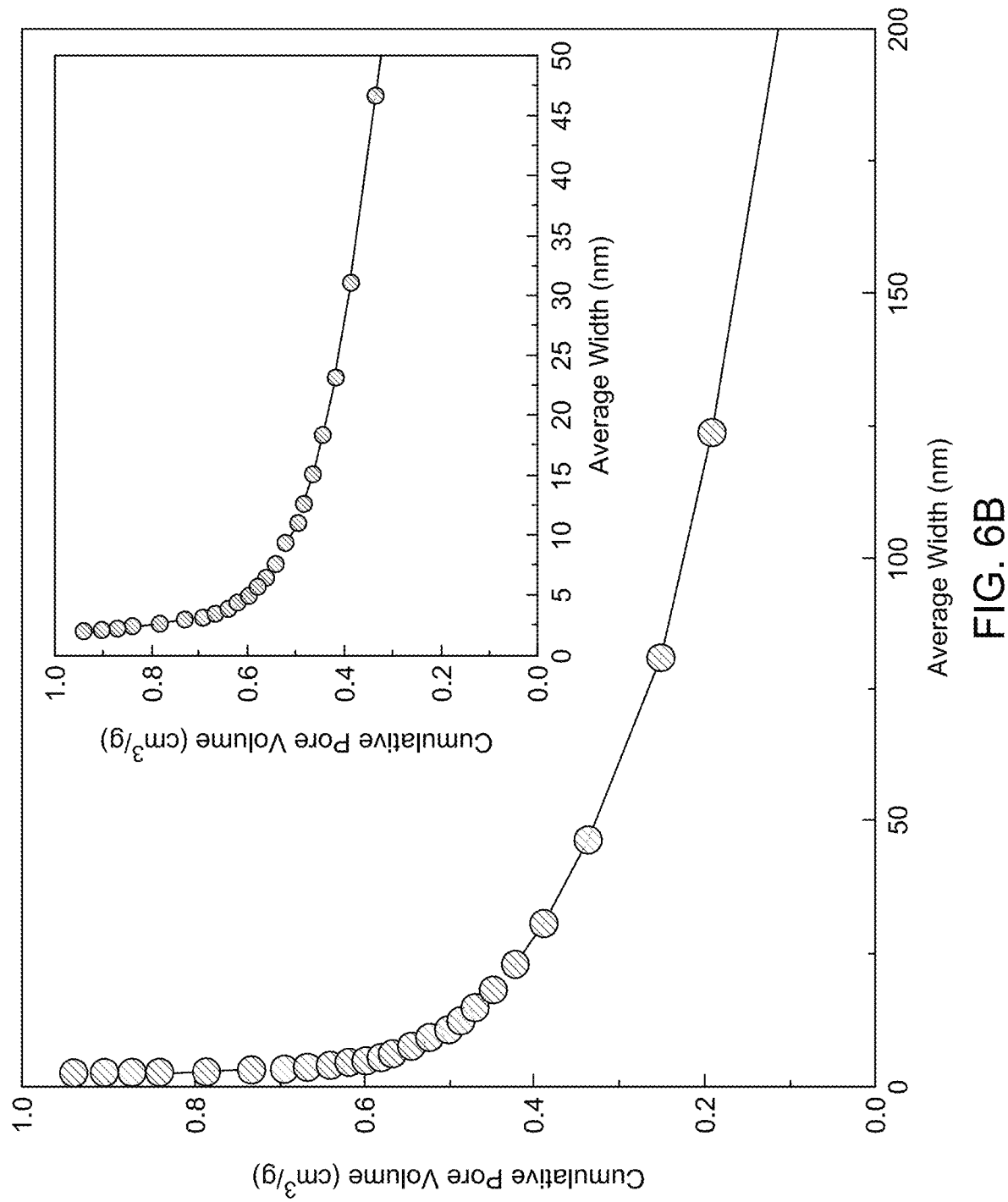
FIG. 6B is a Barrett, Joyner, and Halenda (BJH) pore size distribution curve of the TAC, according to an aspect of the present disclosure.

FIG. 6A and FIG. 6B show the nitrogen adsorption/desorption isotherm as well as the average pore width distribution of the TAC (i.e., Barrett Joyner Halenda (BJH) distribution curve). Referring to FIG. 6A, the TAC exhibited a type IV nitrogen adsorption/desorption isotherm and an H4 hysteresis loop in the range of 0.42 $P/P_o$ to 0.99 $P/P_o$. TAC materials with mixed micropores and mesopores, as well as macropores, have H4-type hysteresis loops. The TAC has a hierarchical porous structure and a large BET SSA of 1440 $m^2/g$. The corresponding BJH pore size distributions for the TAC are shown in FIG. 6B, showing a wide pore size distribution spanning <1 nm to 200 nm. The TAC's vast pore volume distribution shows the dominance of micro- (<1 to 2 nm), meso- (from 2 to 50 nm), and macro- (>50 nm) pores. The inset of FIG. 6B shows a maximized portion of the BJH pore size distribution curve from an average width of 0 to 50 nm for the TAC. The combination of assessable BET SSA and the porous structure is advantageous in developing energy storage devices. Such a combination may promote electrolyte diffusion through the pores to reach the maximum SSA and shorten the electron transport path, thereby enhancing the supercapacitor's charge/discharge process.

Figure 7A:
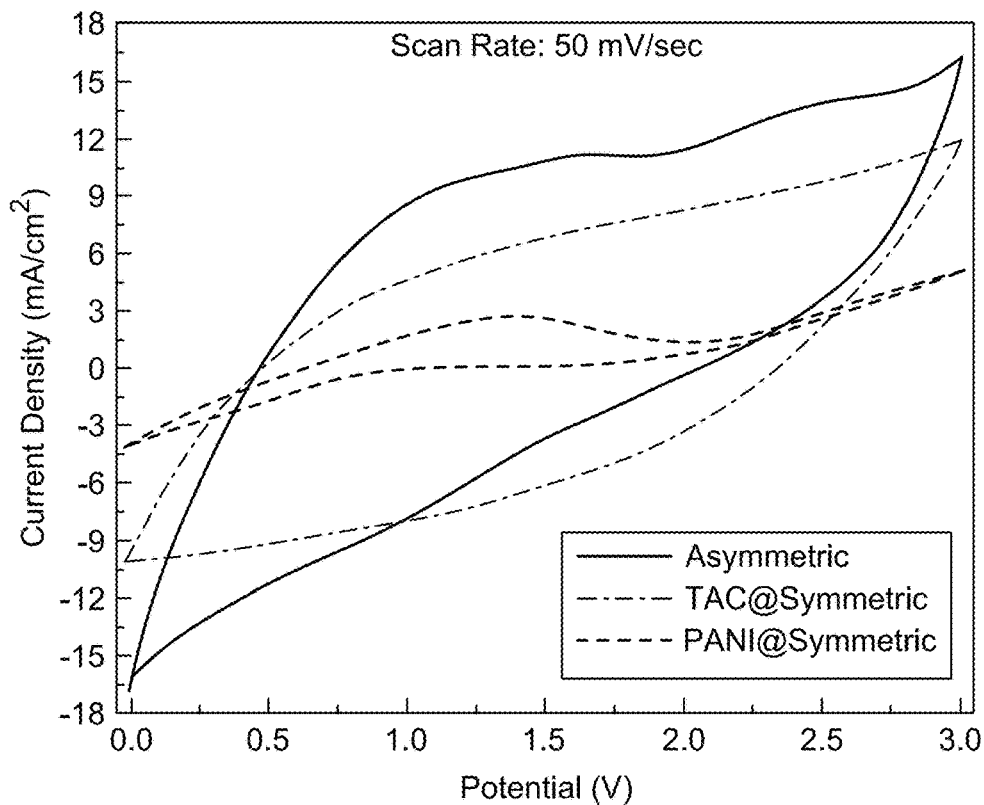
FIG. 7A illustrates cyclic voltammetry (CV) curves of the PANI@symmetric, TAC@symmetric, and asymmetric supercapacitor in the ionic liquid electrolyte at a scan rate of 50 mV/sec, according to an aspect of the present disclosure.

The electrochemical performance comparison of the fabricated PANI@symmetric, TAC@symmetric, and asymmetric supercapacitor was performed in the ionic liquid electrolyte using CC as a current collector. FIG. 7A exhibits overlaid cyclic voltammograms of the PANI@symmetric, TAC@symmetric, and asymmetric supercapacitors performed at a scan rate of 50 mV/sec in an OPW from 0 V to 3.0 V to determine a redox behavior of the electrode materials and to compare overall electrochemical performance. The cyclic voltammogram of the PANI@symmetric supercapacitor shows clear redox peaks between 1.0 V and 2.0 V depicting the pseudocapacitance behavior. Such an oxidation peak and a reduction peak in the PANI@symmetric supercapacitor may be due to: (a) PANI's transition from a reduced leucoemeraldine state to a partially oxidized emeraldine state, (b) PANI's change from the leucoemeraldine state to the pernigraniline state, and (c) PANI's faradic conversion of the emeraldine to pernigraniline redox states [See: S. S. Shah, M. A. Alfasane, I. A. Bakare, M. A. Aziz, Z. H. Yamani, J. Energy Storage 2020, incorporated herein by reference in its entirety]. The PANI@symmetric supercapacitor exhibited a very low current density in the OPW.

The cyclic voltammogram of the TAC@symmetric supercapacitor demonstrates a pure electrochemical double-layer capacitor (EDLC) behavior with no oxidation and reduction peaks. A current density response for the TAC@symmetric supercapacitor was slightly higher than the PANI@symmetric supercapacitor due to a high diffusion of the electrolytes into the TAC pores, which exhibited a high SSA. The structure of the cyclic voltammogram for asymmetric, however, displayed a distinction when compared to an ideal EDLC, with anodic and cathodic peaks between 1.0 V and 2.5 V. The redox peaks with EDLC-type behavior indicated a faradic capacitive characteristic of a hybrid supercapacitor [See: S. S. Shah, M. A. Aziz, A.-R. Al-Betar, W. Mahfoz, Arab. J. Chem. 2022, incorporated herein by reference in its entirety]. Because of TAC and PANI's combined ELDC and pseudocapacitance behavior, the current density response of asymmetric supercapacitors was higher than that of PANI@symmetric supercapacitor and TAC@symmetric supercapacitor. In hybrid supercapacitor-type performance, such behavior demonstrates that the asymmetric supercapacitor outperforms the PANI@symmetric supercapacitor and TAC@symmetric supercapacitor.

Figure 7B:
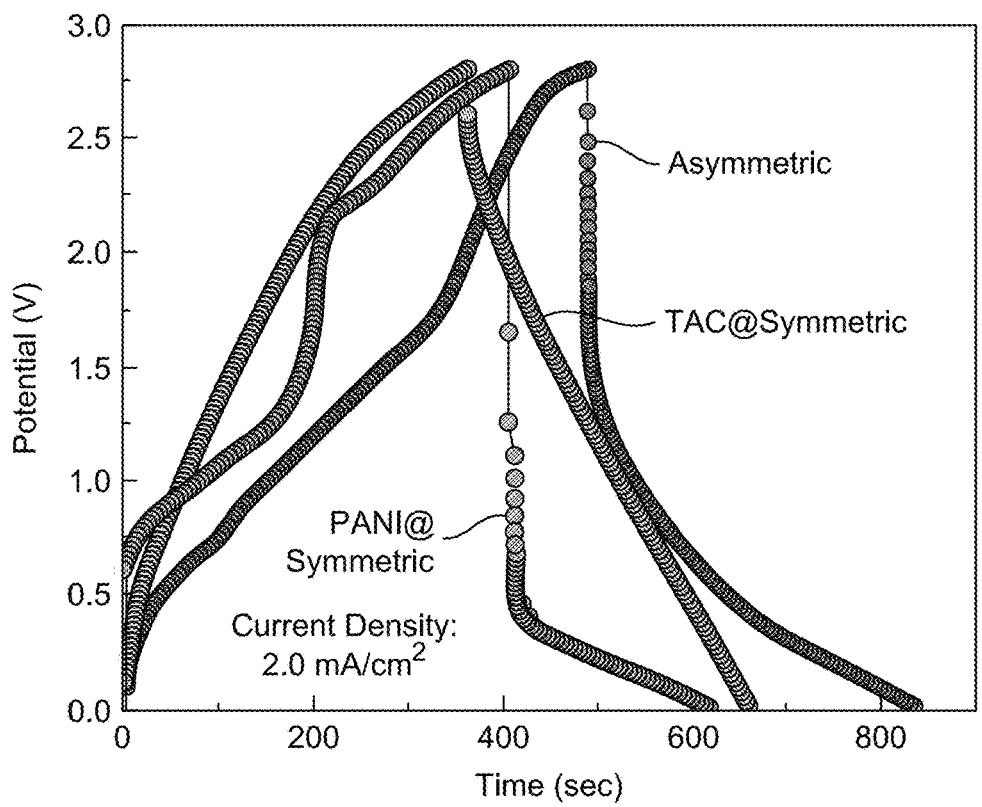
FIG. 7B illustrates galvanostatic charge-discharge (GCD) profiles at a current density of 2.0 mA/cm$^2$ of the PANI@symmetric, TAC@symmetric, and asymmetric supercapacitor in the ionic liquid electrolyte, according to an aspect of the present disclosure.

FIG. 7B depicts the GCD profiles of PANI@symmetric, TAC@symmetric, and asymmetric supercapacitor at a current density of 2.0 $mA/cm^2$ and an OPW of 0 V to 2.8 V. It is shown that the PANI@symmetric supercapacitor has a shorter discharge time and a larger IR drop than TAC@symmetric and asymmetric supercapacitors. IR drop is a potential drop due to a solution resistance. The GCD profile of the TAC@symmetric supercapacitor showed an EDLC-type behavior with an improved discharging time and a more gradual IR drop. However, with the combination of TAC and PANI, the asymmetric supercapacitor resulted in an increase in the discharge time and negligible IR drop, demonstrating the suitability of the asymmetric supercapacitor for electrochemical applications.

Figure 7C:
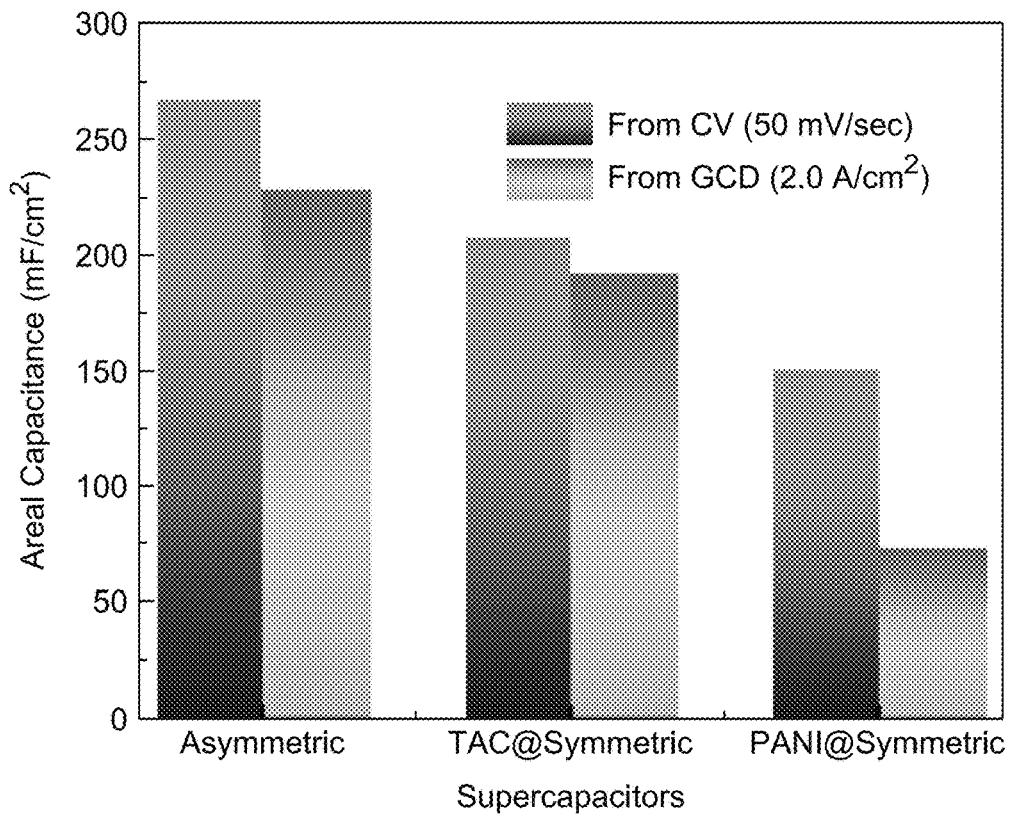
FIG. 7C illustrates bar graphs of corresponding areal capacitance from the CV and the GCD data, according to an aspect of the present disclosure.
Figure 7D:
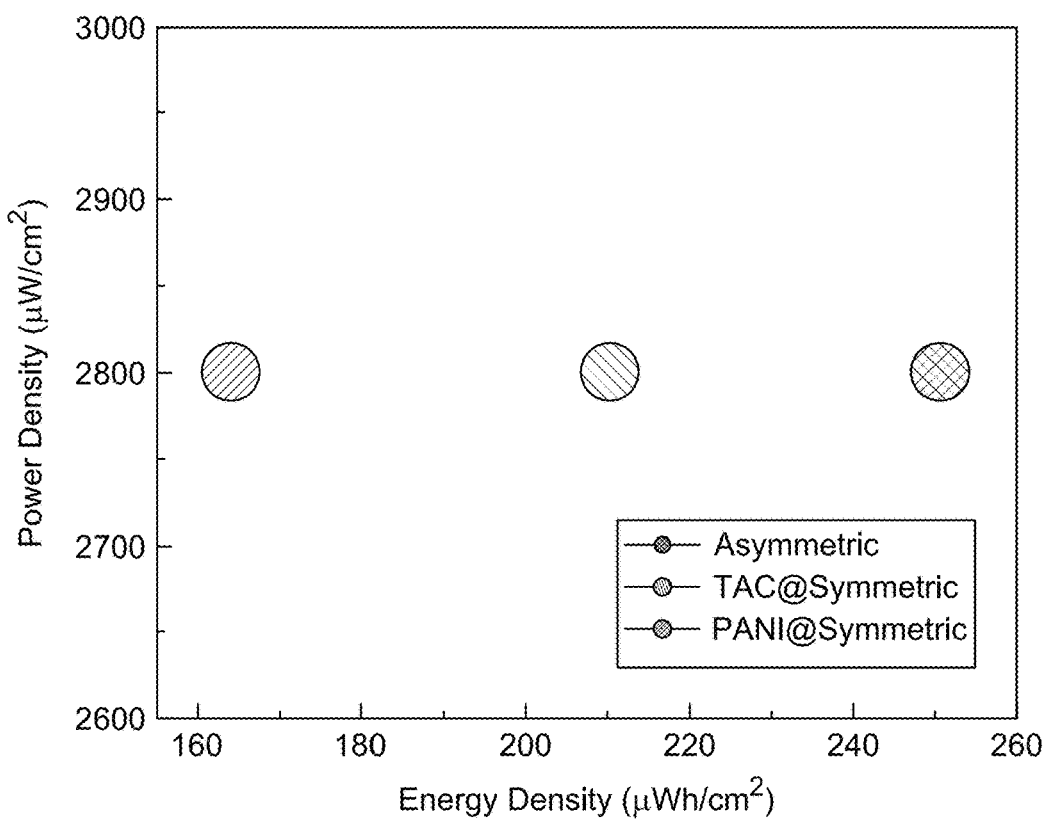
FIG. 7D is a Ragone plot of the PANI@symmetric, TAC@symmetric, and asymmetric supercapacitor in the ionic liquid electrolyte, according to an aspect of the present disclosure.

As shown in FIG. 7C, at a scan rate of 50 mV/sec, the areal capacitances of PANI@symmetric, TAC@symmetric, and asymmetric supercapacitor were 74, 259, and 268 $mF/cm^2$, respectively. At a current density of 2.0 $mA/cm^2$, the areal capacitances of the PANI@symmetric, TAC@symmetric, and asymmetric supercapacitor computed from the GCD data and were found to be 151, 193, and 230 $mF/cm^2$, respectively. This demonstrates a synergistic effect of TAC@CC and PANI@CC in the asymmetric supercapacitor. Similarly, the Ragone plot in FIG. 7D shows that the asymmetric supercapacitor exhibited a higher energy density of 251 $\mu Wh/cm^2$ than the PANI@symmetric (164 $\mu Wh/cm^2$), and TAC@symmetric (210 $\mu Wh/cm^2$) supercapacitors at a power density of 2800 $\mu W/cm^2$. Such behavior of the PANI and TAC-based asymmetric supercapacitor demonstrate the enriched potential in electrochemical energy storage.

The PANI@CC and TAC@CC electrodes were used as the positive and negative electrodes for the asymmetric supercapacitor, respectively. A simple filter paper was used as a separator soaked in the ionic liquid electrolyte. Supercapacitors with an aqueous electrolyte were not able to be widely applied due to their low OPW (i.e., low energy density). Increasing the electrochemical OPW may improve the energy density. The ionic liquid electrolytes possess a large operating potential window compared to aqueous electrolytes. Using the ionic liquid as the electrolyte, the fabricated asymmetric supercapacitor performance was explored. Owing to the favorable structural characteristics, the supercapacitor electrodes based on the TAC had successful electrochemical performance in the ionic liquid electrolyte. It was observed that the cyclic voltammograms and GCD plots of the asymmetric supercapacitor may reach up to 3.0 V and 2.8 V, respectively, exhibiting excellent EDLC and pseudocapacitor behavior.

Figure 8A:
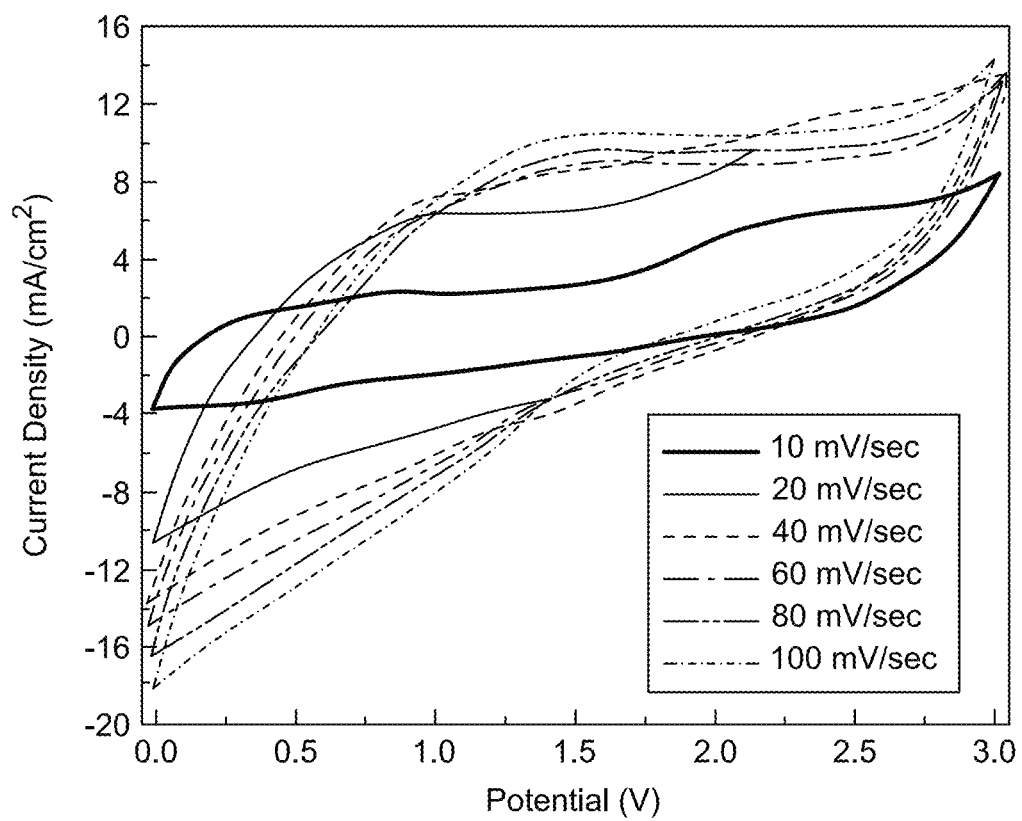
FIG. 8A illustrates cyclic voltammetry (CV) curves of the asymmetric supercapacitor recorded at different scan rates, according to an aspect of the present disclosure.
Figure 8B:
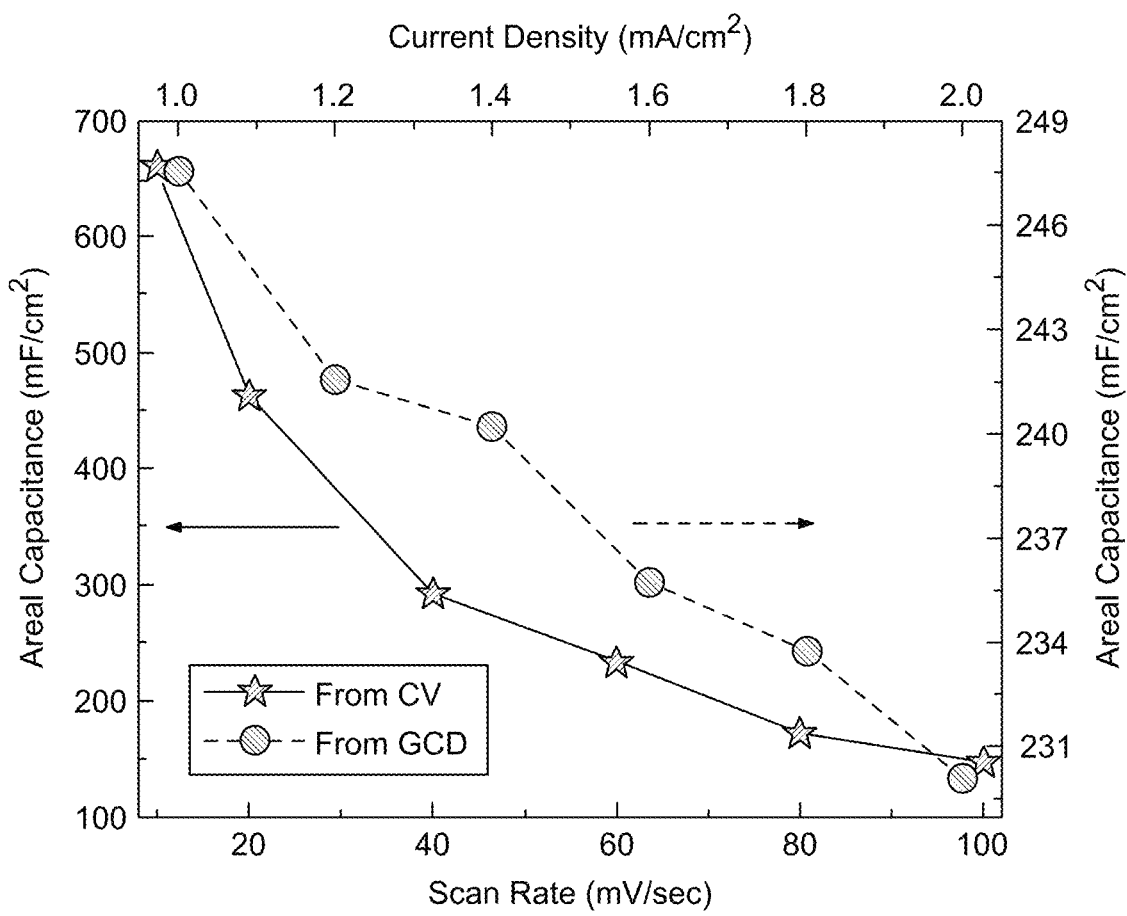
FIG. 8B illustrates areal capacitances obtained from CV of the asymmetric supercapacitor at different scan rates and GCD at different current densities, according to an aspect of the present disclosure.

The cyclic voltammograms at different scan rates for the asymmetric supercapacitor device in the OPW from 0 V to 3.0 V in the ionic liquid electrolyte are shown in FIG. 8A. The cyclic voltammograms of the asymmetric supercapacitor device show a quasi-rectangular shape with redox peaks, exhibiting the hybrid supercapacitor behavior. As may be observed from the voltammograms, the current density and the area under the cyclic voltammograms increases with the increasing scan rates. The areal capacitance decreases from 660 mF/cm² to 146 mF/cm² with increasing scan rate from 10 mV/sec to 100 mV/sec. A decreasing trend in the areal capacitance is shown in FIG. 8B. Such decreasing trend may be due to complete diffusion of electrolyte ions into the electrode material at slower scan rates. As a result, a full active surface of the electrode material may be employed to store charge. At higher scan speeds, however, diffusion inhibits the movement of electrolyte ions, and only an outside active surface may be utilized for charge storage [See: S. S. Shah, E. Cevik, M. A. Aziz, T. F. Qahtan, A. Bozkurt, Z. H. Yamani, Synth. Met. 2021, incorporated herein by reference in its entirety]. This behavior also shows that the asymmetric device allows fast ion diffusion through the pores of the TAC at high rates.

Figure 8C:
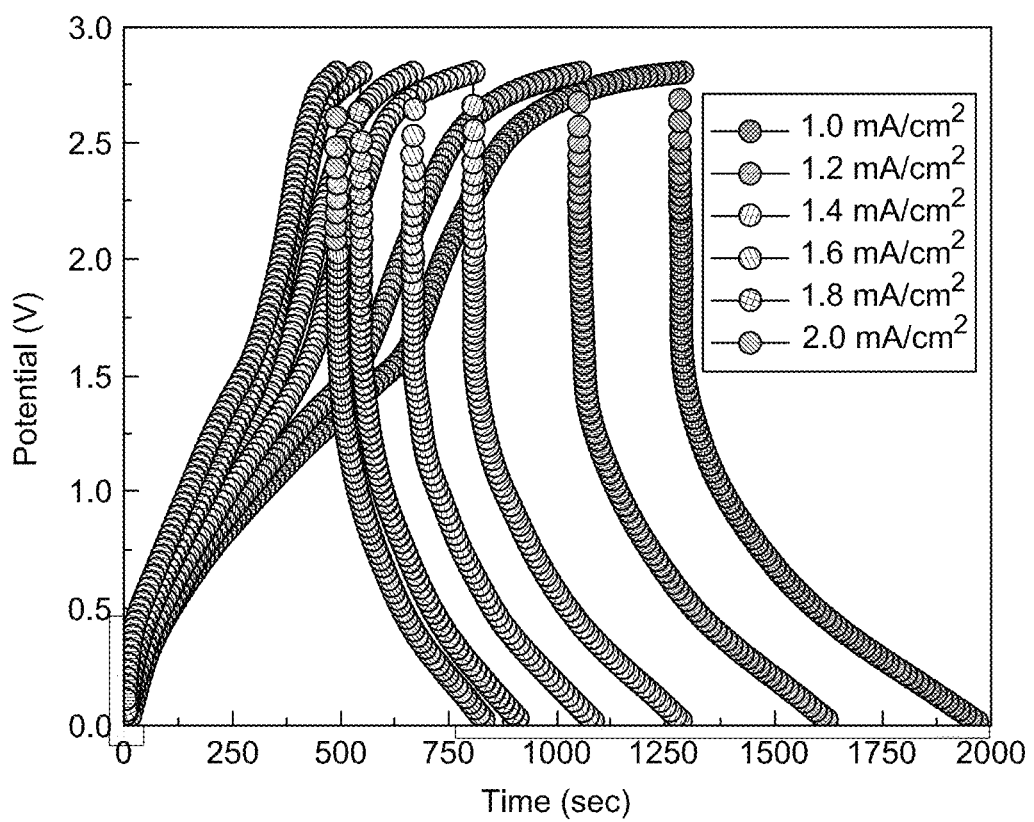
FIG. 8C illustrates GCD profiles of the asymmetric supercapacitor recorded at different current densities, according to an aspect of the present disclosure.

GCD tests were performed at varied current densities from 1.0 mA/cm² to 2.0 mA/cm² in an OPW from 0 V to 2.8 V to understand the electrochemical capacitive capabilities of the asymmetric supercapacitor, and the findings are illustrated in FIG. 8C. As it may be observed from the FIG. 8C, the curves retained the triangle-like form with a curvature showing the combined EDLC and pseudocapacitance nature of the asymmetric supercapacitor and also indicating a long-term behavior in a wide OPW. Furthermore, the asymmetric supercapacitor exhibited negligible IR drop, showing a high conductive nature. Fluctuations of the areal capacitance of the asymmetric supercapacitor with current density are illustrated together in FIG. 8B. It was observed that the specific capacitance dropped as the current density increased. As the current density increased from 1.0 mA/cm² to 2.0 mA/cm², the areal capacitance reduced from 248 mF/cm² to 230 mF/cm².

Figure 8D:
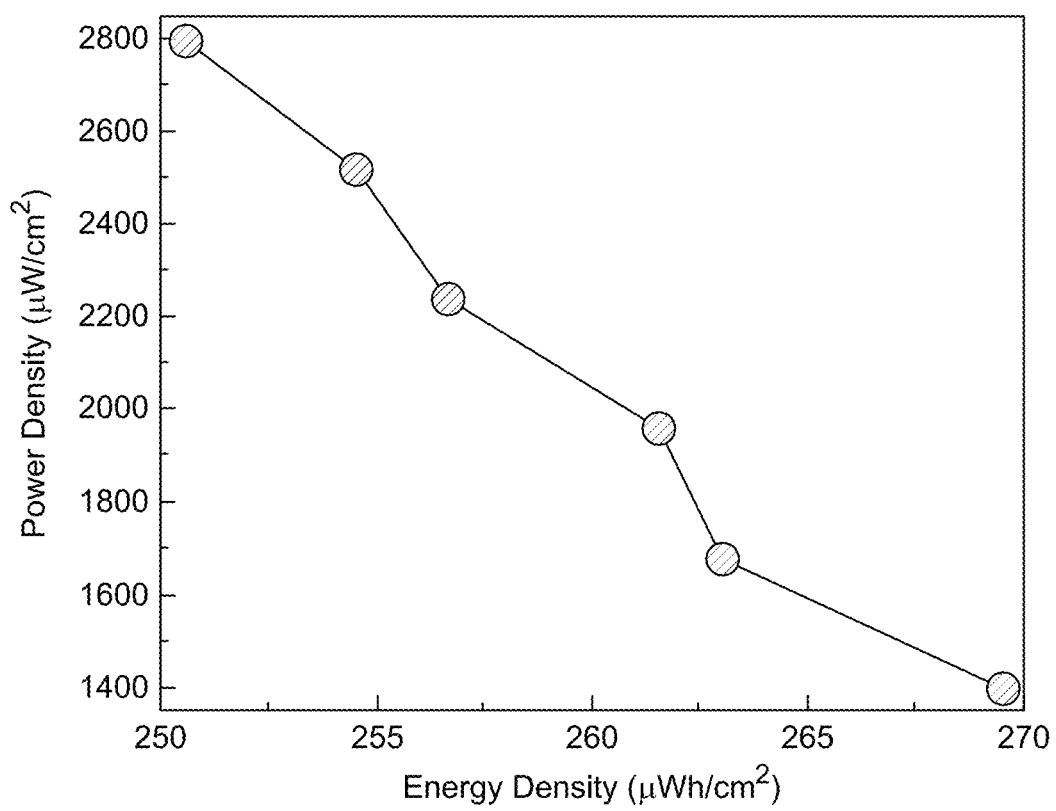
FIG. 8D is a Ragone plot of the asymmetric supercapacitor, according to an aspect of the present disclosure.
Figure 8E:
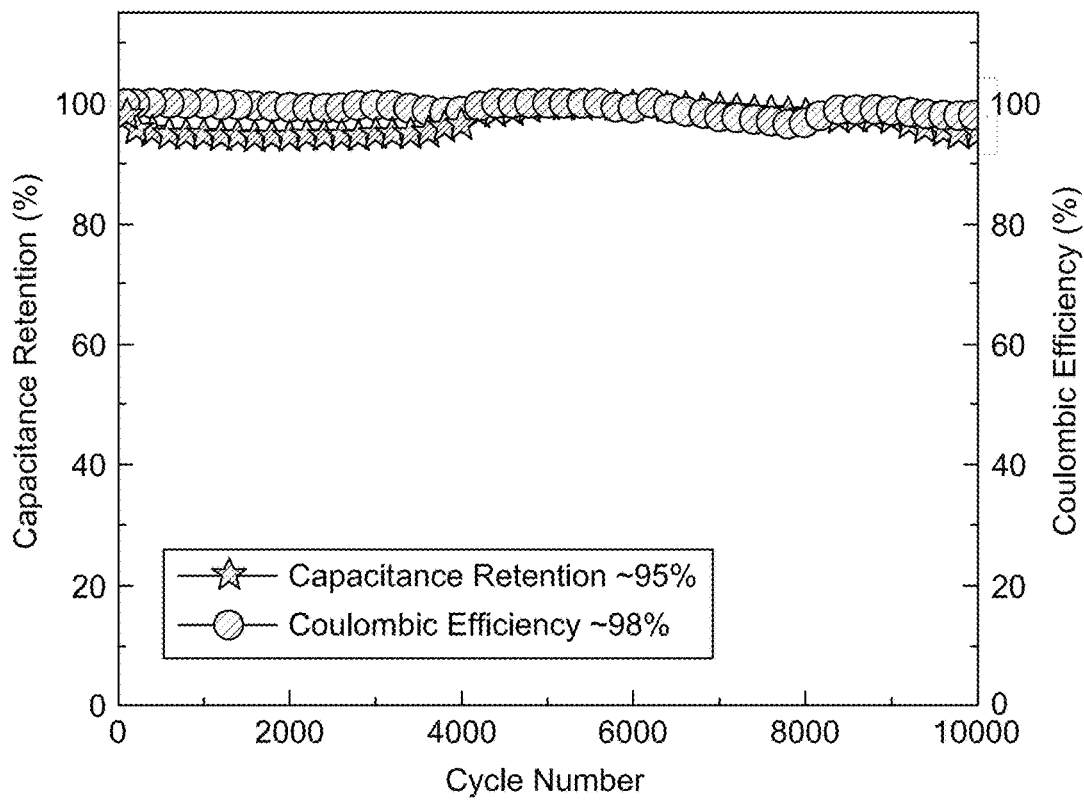
FIG. 8E illustrates capacitance retention and Coulombic efficiency of the asymmetric supercapacitor up to 10000 cycles, according to an aspect of the present disclosure.
Figure 8F:
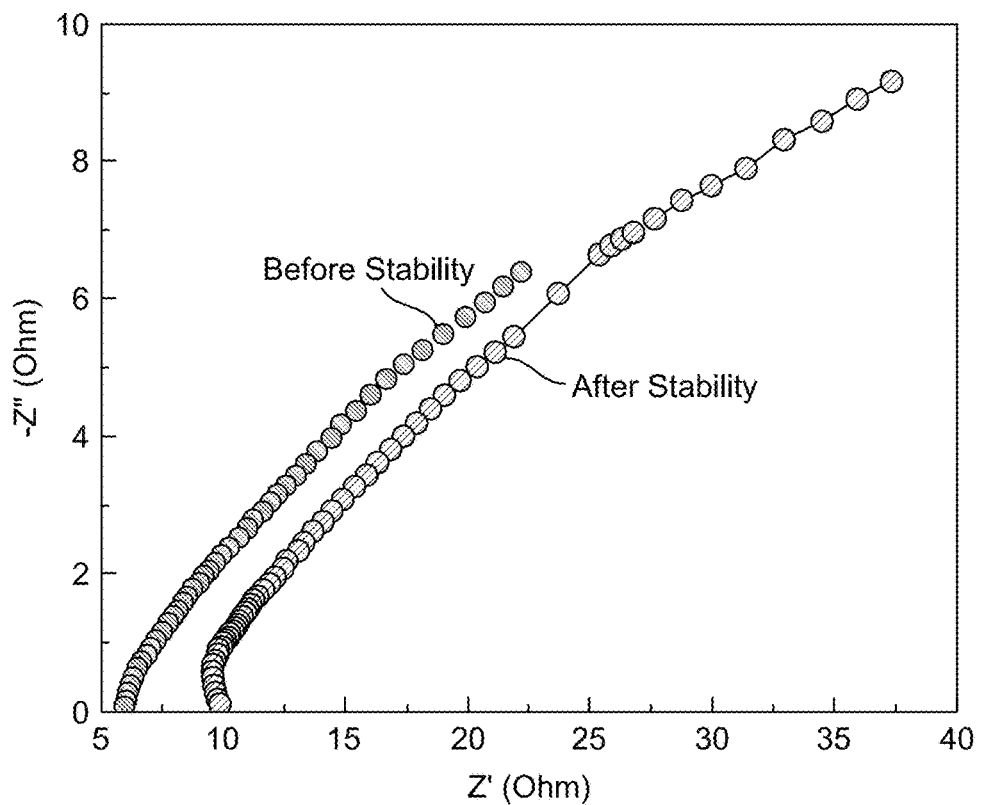
FIG. 8F illustrates Nyquist plots before and after stability of the asymmetric supercapacitor in ionic liquid electrolyte, according to an aspect of the present disclosure.
Figure 8G:
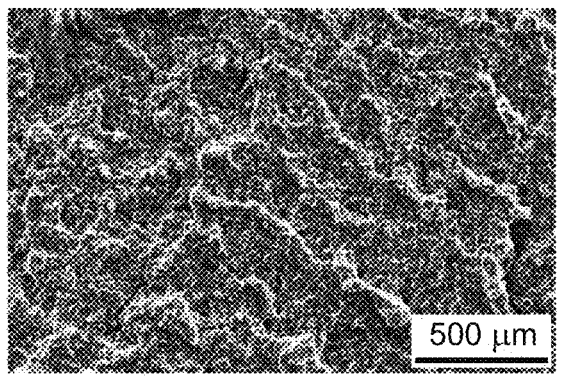
FIG. 8G is the FESEM micrograph of TAC@CC at 100× magnification after long term cyclic stability, according to an aspect of the present disclosure.
Figure 8H:
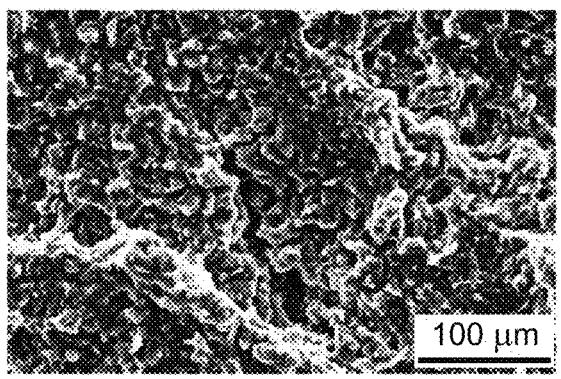
FIG. 8H is the FESEM micrograph of TAC@CC at 500× magnification after long term cyclic stability, according to an aspect of the present disclosure.
Figure 8I:
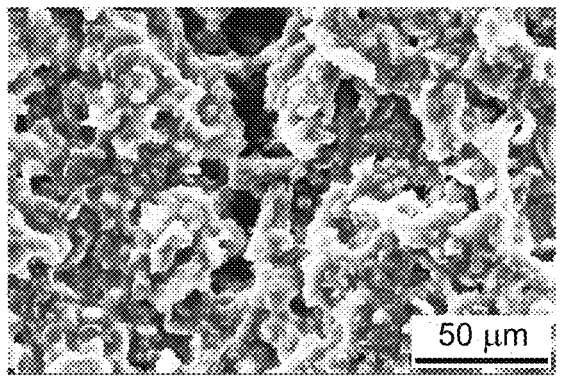
FIG. 8I is the FESEM micrograph of TAC@CC at 1000× magnification after long term cyclic stability, according to an aspect of the present disclosure.
Figure 8J:
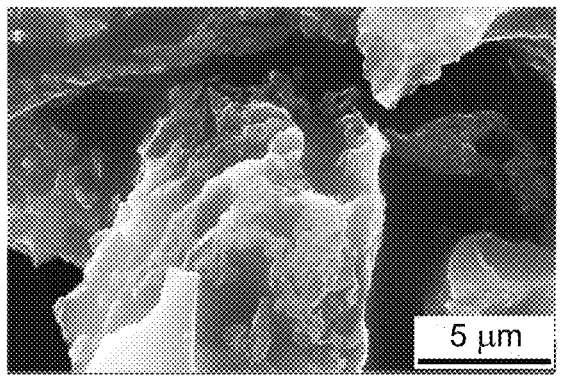
FIG. 8J is the FESEM micrograph of TAC@CC at 10000× magnification after long term cyclic stability, according to an aspect of the present disclosure.
Figure 8K:
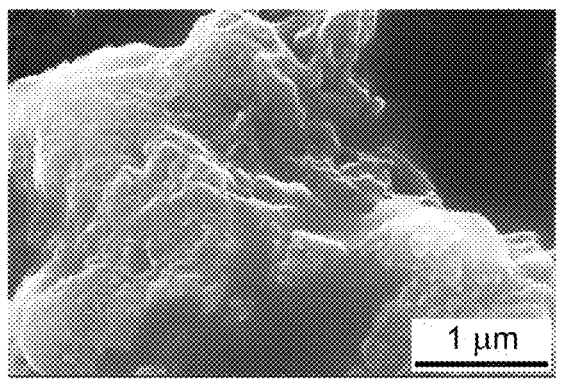
FIG. 8K is the FESEM micrograph of TAC@CC at 50000× magnification after long term cyclic stability, according to an aspect of the present disclosure.
Figure 8L:
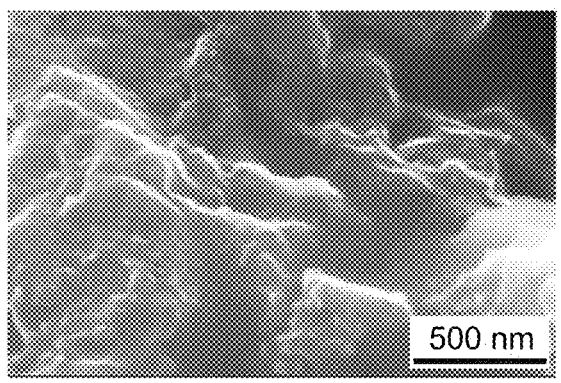
FIG. 8L is the FESEM micrograph of TAC@CC at 100000× magnification after long term cyclic stability, according to an aspect of the present disclosure.

The Ragone plot in FIG. 8D shows the energy and power densities of the asymmetric supercapacitor. The fabricated asymmetric supercapacitor exhibited an ultra-high energy density of 270 μWh/cm² at a power density of 1400 μW/cm² and maintained an energy density of 251 μWh/cm² at a high power density of 2800 μW/cm². As shown in FIG. 8E, the asymmetric supercapacitor shows cyclic stability by maintaining about 95% of its initial capacitance and about 98% of Coulombic efficiency after 10000 charge-discharge cycles at a high current density of 10 mA/cm². These findings revealed that the asymmetric supercapacitor device has good rate capability and sustainability at a large OPW in ionic liquid electrolyte. The Nyquist plots of the asymmetric supercapacitor before and after the cyclic stability (10000 GCD cycles) test are shown in FIG. 8F, which offer an optimum solution resistance (due to the use of ionic liquid electrolyte), low charge transfer resistance, and low Warburg impedance due to the compatibility of PANI and TAC in an asymmetric device. This indicates that the supercapacitor in ionic liquid electrolytes has a low internal resistance, smooth charges of the electron, and enhanced ionic conductivity. Table 1 tabulates the electrochemical impedance spectroscopy (EIS) fitting parameters for the asymmetric supercapacitor before and after cyclic stability (10000 GCD cycles)

TABLE 1

Electrochemical impedance spectroscopy fitting parameters for the asymmetric supercapacitor before and after cyclic stability.

| | $R_{ERS}$ | $R_{CT}$ | $R_L$ | $CPE_{DL}$ | | $CPE_P$ | | $W_O$ | |
|---|---|---|---|---|---|---|---|---|---|
| | (Ω) | (Ω) | (Ω) | Q | n | Q | n | $W_{OR}$ | $W_{OC}$ |
| Before Stability | 5.48 | 1.13 | 432 | 0.027 | 0.42 | 0.05 | 0.48 | 0.7 | 0.3 |
| After Stability | 9.05 | 1.26 | 268 | 0.031 | 0.54 | 0.04 | 0.77 | 0.8 | 0.3 |

As shown in FIG. 8G to FIG. 8L, FESEM images of the TAC@CC after long term cyclic stability (10000 GCD cycles) demonstrate no degradation of the TAC@CC (See FIG. 2I to FIG. 2L for comparison). The porous nanosheet-type morphology of the prepared TAC@CC after long term cyclic stability is seen in FIG. 8G to FIG. 8L. The electrochemical performance comparison of the fabricated TAC and PANI based asymmetric supercapacitor with asymmetric supercapacitors reported in literature is tabulated in Table 2.

TABLE 2

Electrochemical performance comparison of the fabricated TAC and PANI based symmetric and asymmetric supercapacitors with supercapacitors reported in the literature.

| Positive Electrode | Negative Electrode | Supercapacitor type | Electrolyte | Capacitance | Energy Density μWh/cm² | Power Density μW/cm² | Capacitance Retention (%, No. of Cycles) |
|---|---|---|---|---|---|---|---|
| PANI@CC* | TAC@CC | Asymmetric | 1-butyl-3-methyl-imidazolium hexafluoro-phosphate | 248 mF/cm² at 1.0 mA/cm² | 270 | 1400 | 95, 10000 |
| PANI@NF[1] | JAC@NF | Asymmetric | 3M KOH | 555 mF/cm² at 0.5 mA/cm² | 77 | 357 | 86, 1000 |
| PANI@ITONPs@FTO[2] | JAC@FTO | Asymmetric | 0.1M HCl | 318 mF/cm² at 1.0 mA/cm² | 28 | 400 | 91, 1000 |
| CFY@CNFs@PANI[3] | CFY@CNFs | Asymmetric | $EMIMBF_4$ | 234 mF/cm² at 0.1 mA/cm² | 21 | 0.52 | 90, 8000 |
| PANI@SP[4] | PANI@SP | Symmetric | $PVA/H_2SO_4$ | 149.3 F/g at 0.5 mA/cm² | 13.0 | 0.40 | 81.2, 5000 |
| PANI[5] | GQDs | Asymmetric | $H_3PO_4$-PVA | 210 μF/cm² at 15.0 μA/cm² | 0.029 | 7.46 | 85.6, 1500 |

TABLE 2-continued

Electrochemical performance comparison of the fabricated TAC and PANI based symmetric
and asymmetric supercapacitors with supercapacitors reported in the literature.

| Positive Electrode | Negative Electrode | Supercapacitor type | Electrolyte | Capacitance | Energy Density $\mu Wh/cm^2$ | Power Density $\mu W/cm^2$ | Capacitance Retention (%, No. of Cycles) |
|---|---|---|---|---|---|---|---|
| PANI@CC* | PANI@CC | Symmetric | 1-butyl-3-methyl-imidazolium hexafluoro-phosphate | 151 $mF/cm^2$ at 2.0 $mA/cm^2$ | 164 | 2800 | — |
| TAC@CC* | TAC@CC | Symmetric | 1-buty1-3-methyl-imidazolium hexafluoro-phosphate | 193 $mF/cm^2$ at 2.0 $mA/cm^2$ | 210 | 2800 | — |
| PANI@GP[6] | PANI@GP | Symmetric | PVA/$H_2SO_4$ | 176 $mF/cm^2$ at 0.2 $mA/cm^2$ | 17.1 | 250 | 74.8, 500 |
| $MnO_2$[7] | $MnO_2$ | Symmetric | 0.1M $NaNO_3$ | 56.3 $mF/cm^2$ at 27.2 $\mu A/cm^2$ | 5010 | 12020 | 72.5, 1000 |
| Graphene[8] | Graphene | Symmetric | PVA/KOH gel electrolyte | 6.7 $F/cm^2$ at 5 $mA/cm^2$ | 520 | 3770 | 109, 40000 |

*Corresponds to work of the present disclosure;
[1]corresponds to S. S. Shah, H. T. Das, H. R. Barai, M. A. Aziz, *Polymers* 2022, 14, 270, incorporated herein by reference in its entirety;
[2]corresponds to S. S. Shah, M. A. Aziz, A.-R. Al-Betar, W. Mahfoz, *Arab. J. Chem.* 2022, 15, 104058, incorporated herein by reference in its entirety;
[3]corresponds to N. Mao, W. Chen, J. Meng, Y. Li, K. Zhang, X. Qin, H. Zhang, C. Zhang, Y. Qiu, S. Wang, *J. Power Sources* 2018, 399, 406-413, incorporated herein by reference in its entirety;
[4]corresponds to L. Hou, X. Zhi, W. Zhang, H. Zhou, *J. Electroanal. Chem.* 2020, 863, 114064, incorporated herein by reference in its entirety;
[5]corresponds to W. Liu, X. Yan, J. Chen, Y. Feng, Q. Xue, *Nanoscale* 2013, 5, 6053-6062, incorporated herein by reference in its entirety;
[6]corresponds to K. Li, X. Liu, S. Chen, W. Pan, J. Zhang, *J. Energy Chem.* 2019, 32, 166-173, incorporated herein by reference in its entirety;
[7]corresponds to X. Wang, B. D. Myers, J. Yan, G. Shekhawat, V. Dravid, P. S. Lee, *Nanoscale* 2013, 5, 4119-4122, incorporated herein by reference in its entirety; and
[8]corresponds to L. Sheng, J. Cheng, L. Jiang, Z. Jiang, Z. Liu, T. Wei, Z. Fan, *Adv. Funct. Mater.* 2018, 28, 1800597, Incorporated herein by reference in its entirety.

Figure 9:
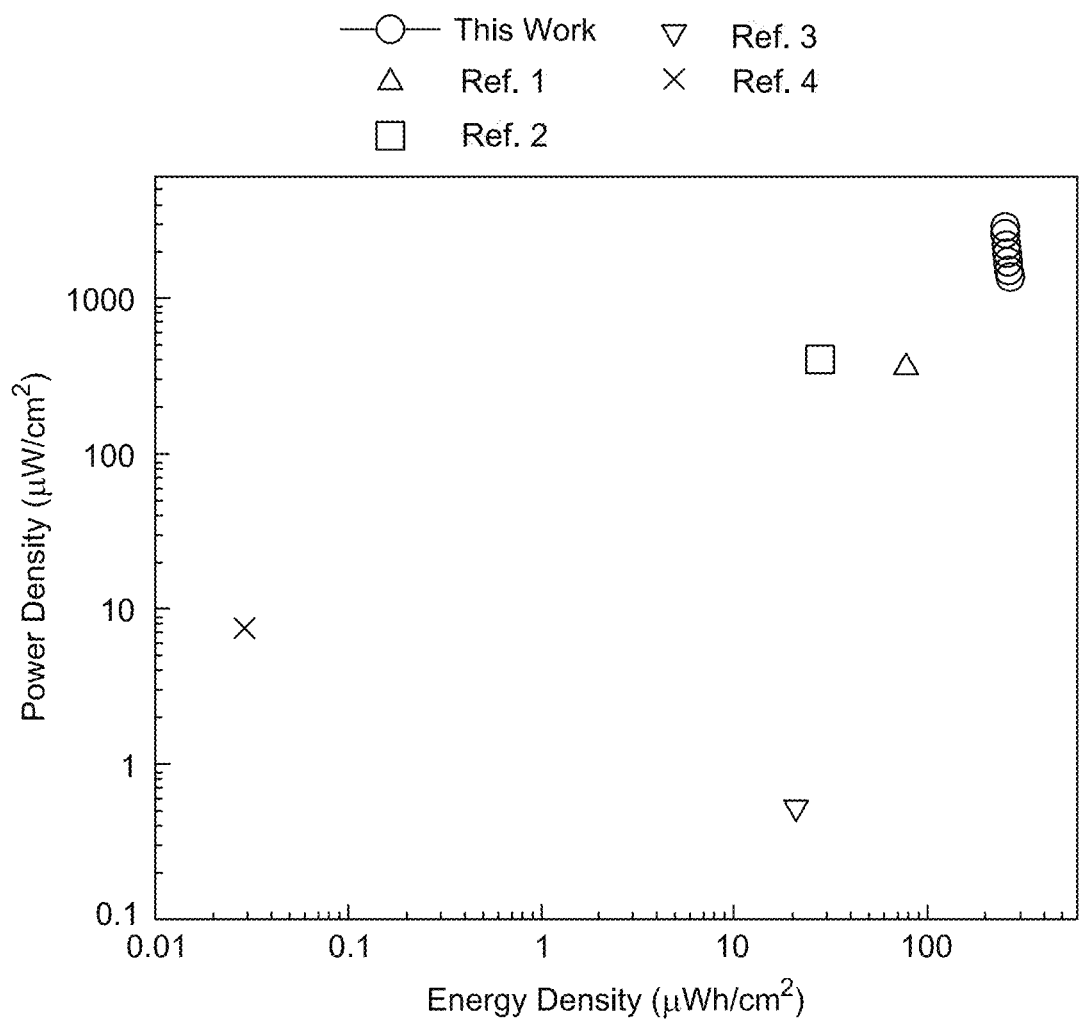
FIG. 9 is a Ragone plot of the asymmetric supercapacitor compared with asymmetric supercapacitors reported in the literature, according to an aspect of the present disclosure

FIG. 9 depicts a Ragone plot of the asymmetric supercapacitor with PANI@CC as the positive electrode, TAC@CC as the negative electrode, and 1-butyl-3-methylimidazolium hexafluorophosphate as the ionic liquid electrolyte with asymmetric supercapacitors reported in the literature. 'This Work' corresponds to work of the present disclosure; 'Ref. 1' corresponds to S. S. Shah, H. T. Das, H. R. Barai, M. A. Aziz, *Polymers* 2022, 14, 270, incorporated herein by reference in its entirety: 'Ref. 2' corresponds to S. S. Shah, M. A. Aziz, A.-R. Al-Betar, W. Mahfoz, *Arab. J. Chem.* 2022, 15, 104058, incorporated herein by reference in its entirety; 'Ref. 3' corresponds to N. Mao, W. Chen, J. Meng, Y. Li, K. Zhang, X. Qin, H. Zhang, C. Zhang, Y. Qiu, S. Wang, *J. Power Sources* 2018, 399, 406-413, incorporated herein by reference in its entirety: 'Ref. 4' corresponds to W. Liu, X. Yan, J. Chen, Y. Feng, Q. Xue, *Nanoscale* 2013, 5, 6053-6062.

Figure 10A:
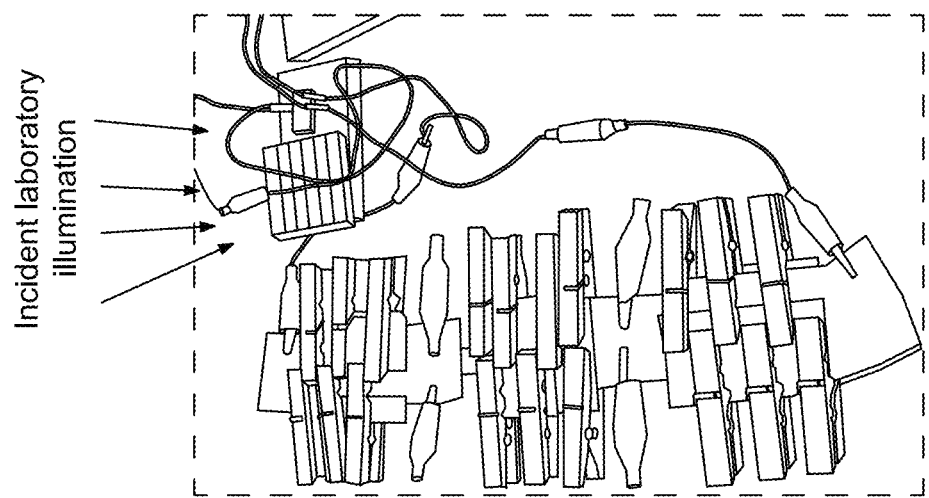
FIG. 10A is a practical demonstration of a developed asymmetric supercapacitor showing assembly of three series connected asymmetric supercapacitors connected to a solar plate for charging, according to an aspect of the present disclosure.
Figure 10B:
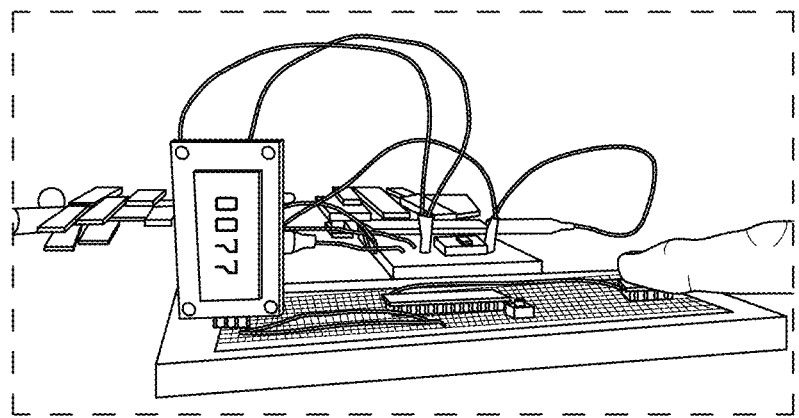
FIG. 10B illustrates a heart pulse rate monitor connected to the asymmetric supercapacitors and testing heart pulse rate after 1 minute, according to an aspect of the present disclosure.
Figure 10C:
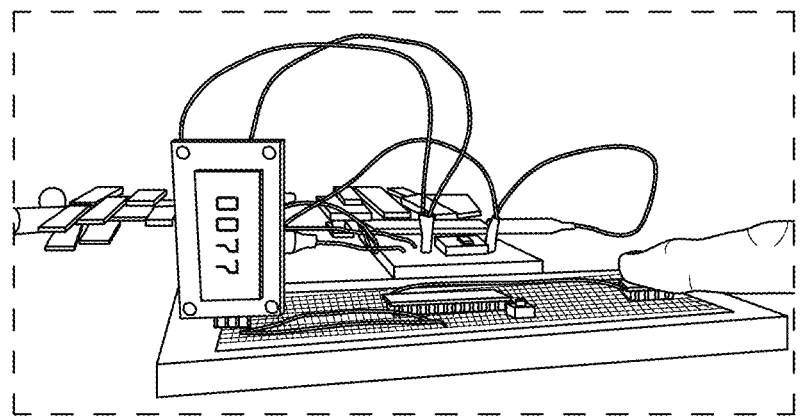
FIG. 10C illustrates the heart pulse rate monitor connected to the asymmetric supercapacitors and testing heart pulse rate after 2 minutes, according to an aspect of the present disclosure.
Figure 10D:
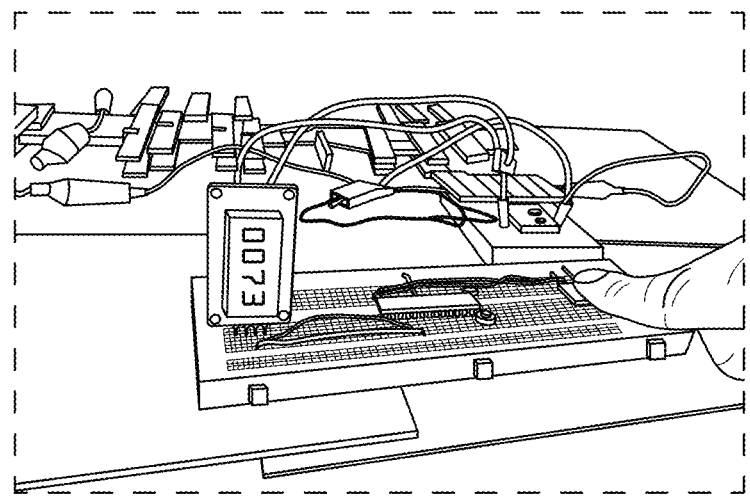
FIG. 10D illustrates the heart pulse rate monitor connected to the asymmetric supercapacitors and testing heart pulse rate after 4 minutes, according to an aspect of the present disclosure.
Figure 10E:
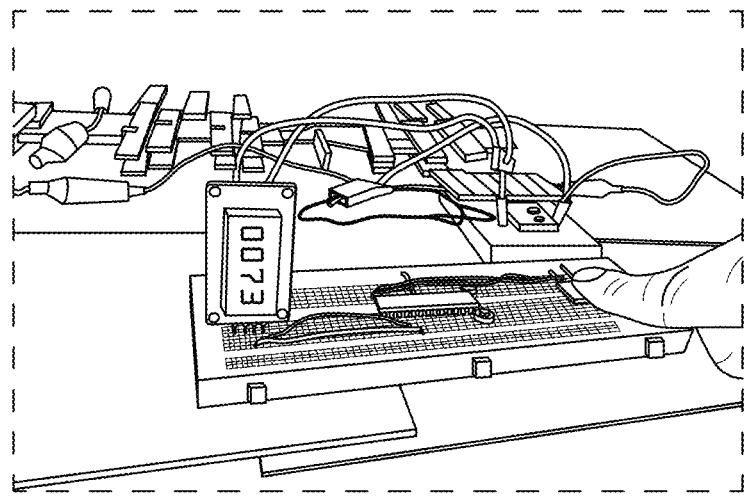
FIG. 10E illustrates the heart pulse rate monitor connected to the asymmetric supercapacitors and testing heart pulse rate after 8 minutes, according to an aspect of the present disclosure.
Figure 10F:
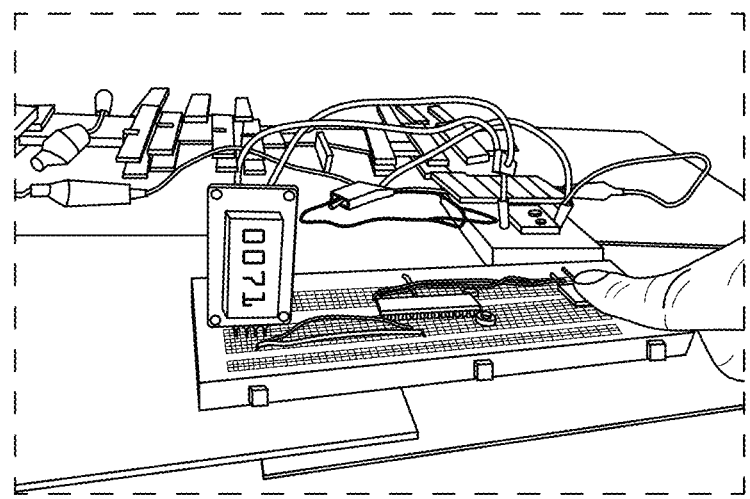
FIG. 10F illustrates the heart pulse rate monitor connected to the asymmetric supercapacitors and testing heart pulse rate after 12 minutes, according to an aspect of the present disclosure.
Figure 10G:
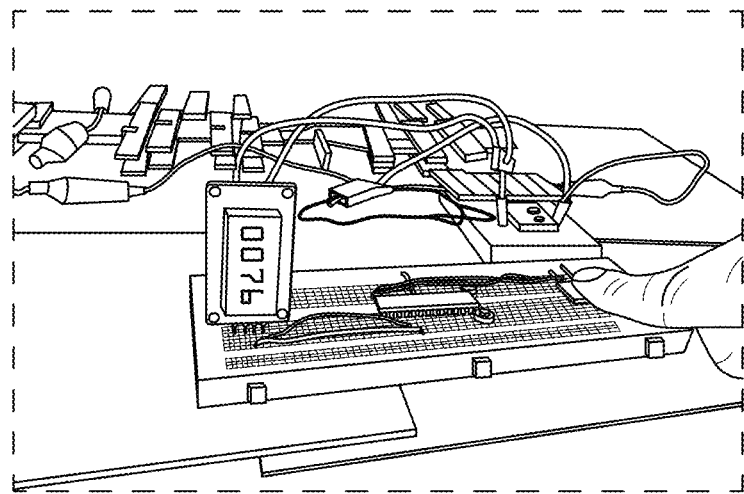
FIG. 10G illustrates the heart pulse rate monitor connected to the asymmetric supercapacitors and testing heart pulse rate after 15 minutes, according to an aspect of the present disclosure.
Figure 10H:
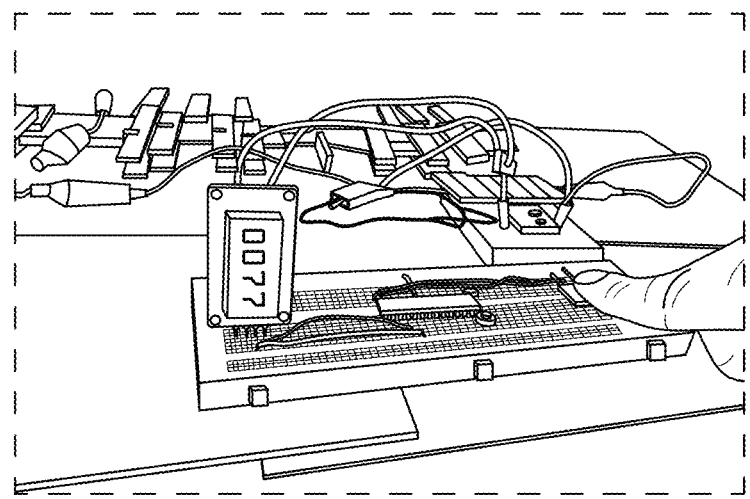
FIG. 10H illustrates the heart pulse rate monitor connected to the asymmetric supercapacitors and testing heart pulse rate after 16 minutes, according to an aspect of the present disclosure.
Figure 10I:
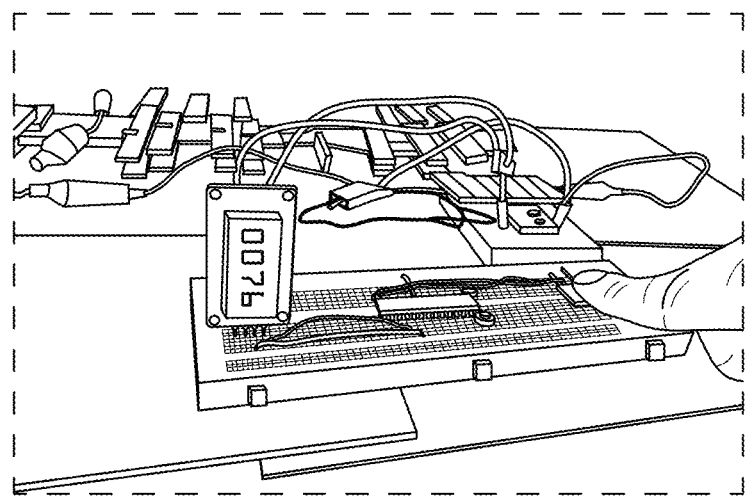
FIG. 10I illustrates the heart pulse rate monitor connected to the asymmetric supercapacitors and testing heart pulse rate after 18 minutes, according to an aspect of the present disclosure.

In addition, the asymmetric supercapacitor based on TAC and PANI electrodes was evaluated to operate a battery-less heart pulse rate monitoring system 1000 (see FIG. 11) as evidence for the practical use of the developed supercapacitor. For practical application, the monitoring system was implemented using a low-power ATmeag328P microcontroller (available from Microchip Technology Inc., Arizona, USA) which was programmed to read the pulse rate from an infrared (IR) sensor. Three asymmetric supercapacitors were connected in series and charged by a solar panel using an ordinary lab light source, as shown in FIG. 10A. A charge controller based on an AEM10941 chip (a Solar Energy Harvesting IC available from Mouser Electronics, Texas, USA) was also used to maintain the charging/discharging operation and prevent possible overflow or in-rush current shoot-through. The developed asymmetric supercapacitors exhibited a remarkable performance by operating the heart pulse rate monitor for around 1 minute. The asymmetric supercapacitor was continuously operating the heart pulse rate monitor when connected to the solar panel and under the light. The corresponding illustrations of the continuous operation for 20 minutes are shown in FIG. 10B through FIG. 10I. Such performance of the asymmetric supercapacitor based on TAC and PANI electrodes in ionic liquid electrolyte demonstrate practical applications for various electronic industries.

Figure 11:
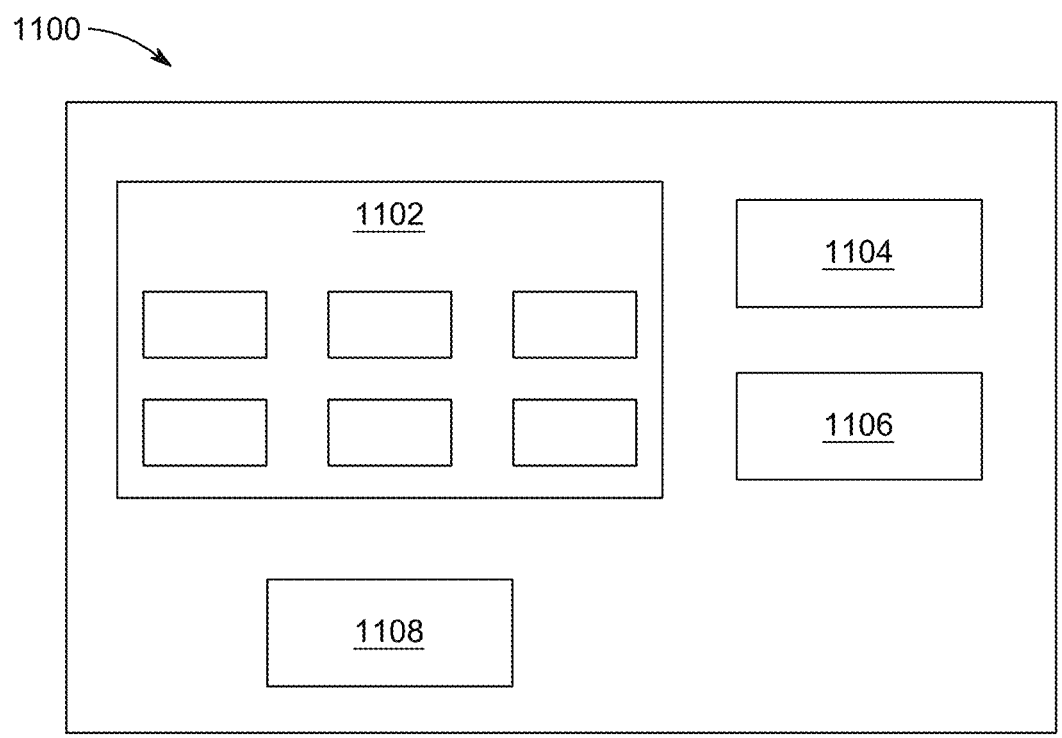
FIG. 11 is an exemplary block diagram of a heart pulse rate monitoring system, according to an aspect of the present disclosure.

Referring to FIG. 11, in an embodiment, the heart pulse rate monitoring system 1000 includes one or more asymmetric supercapacitors 1002 (as described hereinabove), a microcontroller 1004, a sensor 1006, and a charge controller 1008. In some embodiments, the charge controller 1008 may be a solar panel, a solar energy harvesting chip, or a combination thereof. In some embodiments, the heart pulse rate monitoring system 1000 may be configured to operate continuously for at least 20 minutes. The term "microcontroller" as used herein refers to a computer component adapted to control a system to achieve certain desired goals and objectives. For example, the microcontroller may refer to, be part of, or include: an Application Specific Integrated Circuit (ASIC); a digital, analog, or mixed analog/digital discrete circuit; a digital, analog, or mixed analog/digital integrated circuit: a combinational logic circuit: a field programmable gate array (FPGA): a processor circuit (shared, dedicated, or group) that executes code: a memory circuit (shared, dedicated, or group) that stores code executed by the processor circuit: other suitable hardware components that provide the described functionality; or a combination of some or all of the above, such as in a system-on-chip. The term "sensor" refers, without limitation, to the component or region of a device which is configured to detect the presence or absence of a measurable parameter. For example, a camera sensor may be a camera configured to capture images or frames.

To this end, the present disclosure provides a high energy density asymmetric supercapacitor fabricated using tomato leaves-derived hierarchical porous activated carbon (TAC) and PANI as both negative and positive electrodes in ionic liquid electrolyte, respectively. In comparison to the symmetric supercapacitors using purely TAC or PANI electrodes, the assembled asymmetric supercapacitor exhibits an areal capacitance of 230 mF/cm$^2$ at a current density of 2.0 mA/cm$^2$, while the symmetric supercapacitors using pure TAC or PANI electrodes show areal capacitances of 151 mF/cm$^2$, 193 mF/cm$^2$ at the same current density, respectively. In addition, the developed asymmetric supercapacitor was able to deliver a high specific capacitance of and 248 mF/cm$^2$ in ionic liquid electrolyte at a current density of 1.0 mA/cm$^2$. Furthermore, after 10,000 charge-discharge cycles, the asymmetric supercapacitor displayed a high energy density of 270 μWh/cm$^2$ while having a high power density of 1400 μW/cm$^2$. Additionally, the asymmetric supercapacitor exhibited cyclic stability of about 95% capacitance retention of an initial capacitance value and about 98% Coulombic efficiency. The series of connected assembled asymmetric supercapacitors based on TAC and PANI electrodes performed in operating the heart pulse rate monitor upon charging via a solar panel and using laboratory illumination.

Numerous modifications and variations of the present disclosure are possible in light of the above teachings. It is, therefore, to be understood that, within the scope of the appended claims, the disclosure may be practiced otherwise than as specifically described herein.

The invention claimed is:
1. An asymmetric supercapacitor, comprising:
a negative electrode comprising a tomato leaf activated carbon having a hierarchical porosity disposed on a first carbon cloth;
a positive electrode comprising a polyaniline disposed on a second carbon cloth;
an ionic liquid electrolyte; and
a separator,
wherein the separator is between the positive electrode and the negative electrode, and the electrolyte is present in and on the separator.
2. The supercapacitor of claim 1, wherein the tomato leaf activated carbon has a specific surface area of 1400 m$^2$/g to 1500 m$^2$/g.
3. The supercapacitor of claim 1, wherein the tomato leaf activated carbon is in the form of nanosheets having a pore size distribution of 1 nm to 200 nm.
4. The supercapacitor of claim 1, wherein the negative electrode is made by a process comprising:
rinsing tomato leaves;
drying the tomato leaves;
pulverizing the tomato leaves;
mixing the tomato leaves with a base to form a first reaction mixture;
heating the first reaction mixture in a tube furnace at 850° C. for at least 5 hours under a nitrogen atmosphere with a heating rate of 10° C./minute and a cooling rate of 5° C./minute to form a reaction product;
washing the reaction product;
drying the reaction product to form the tomato leaf activated carbon;
sonicating the tomato leaf activated carbon in solution with a polyvinylidene fluoride polymer and an N-methyl-2-pyrrolidone to form a second reaction mixture;
drop-casting the second reaction mixture onto the first carbon cloth and drying to form the negative electrode.
5. The process of claim 4, wherein a ratio of the tomato leaf activated carbon to the polyvinylidene fluoride in the N-methyl-2-pyrrolidone is 85:15 percent weight by weight to 95:5 percent weight by weight.
6. The process of claim 4, wherein a working area of drop-casting the second reaction mixture onto the first carbon cloth is 0.5 cm$^2$ to 1.5 cm$^2$.
7. The supercapacitor of claim 1, wherein the polyaniline on the second carbon cloth has a nodular morphology with void spaces having an average diameter of 5 μm to 500 μm and polyaniline nanoparticles having an average diameter of 0.05 μm to 0.5 μm uniformly distributed on carbon cloth fibers having an average diameter of 1 μm to 10 μm.
8. The supercapacitor of claim 1, wherein the positive electrode is made by a process comprising:
electrodepositing the polyaniline on the second carbon cloth with cyclic voltammetry for 15 cycles at a scan rate of 50 mV/sec in a window of 0.0 V to 1.0 V vs Ag/AgCl;
rinsing the polyaniline on the second carbon cloth; and
drying the polyaniline on the second carbon cloth,
wherein the solution comprises aniline and sulfuric acid.
9. The process of claim 8, wherein the electrodepositing includes electrodepositing the polyaniline on a target area of the second carbon cloth of 0.5 cm$^2$ to 1.5 cm$^2$.
10. The supercapacitor of claim 1, wherein the ionic liquid electrolyte is 1-butyl-3-methylimidazolium hexafluorophosphate.
11. The supercapacitor of claim 1, wherein a first electrode is the negative electrode comprising a tomato leaf activated carbon having a hierarchical porosity disposed on the first carbon cloth and a second electrode is the positive electrode comprising a polyaniline disposed on the second carbon cloth.
12. The supercapacitor of claim 1, wherein the separator is a cellulose membrane soaked in the ionic liquid electrolyte.
13. The supercapacitor of claim 1, wherein the supercapacitor has an areal capacitance of 230 mF/cm$^2$ to 270 mF/cm$^2$ at a scan rate of 50 mV/sec.
14. The supercapacitor of claim 1, wherein the supercapacitor has an energy density of 240 μWh/cm$^2$ to 280 μWh/cm$^2$ at a power density of 1300 μW/cm$^2$ to 2900 μWh/cm$^2$.
15. The supercapacitor of claim 1, wherein the supercapacitor has a capacitance retention after 10,000 charge-discharge cycles of at least 95% of a first charge-discharge cycle.
16. The supercapacitor of claim 1, wherein the supercapacitor has a Coulombic efficiency of at least 98% after 10,000 charge-discharge cycles at a current density of 10 mA/cm$^2$.
17. The supercapacitor of claim 1, wherein an operating potential window is from −0.5 V to 3.5 V.
18. A heart pulse rate monitoring system, comprising:
one or more of the supercapacitor of claim 1;
a microcontroller;
a sensor; and
a charge controller.

19. The heart pulse rate monitor system of claim 18, wherein the charge controller is a solar panel, a solar energy harvesting chip, or a combination thereof.

20. The heart pulse rate monitoring system of claim 18, wherein the system operates continuously for at least 20 minutes.

* * * * *